United States Patent
Smirnov et al.

(10) Patent No.: US 12,104,193 B2
(45) Date of Patent: Oct. 1, 2024

(54) METHOD FOR ENZYMATIC SULFURYLATION OF ALCOHOLS AND AMINES USING BACTERIUM OF THE FAMILY ENTEROBACTERIACEAE

(71) Applicant: AJINOMOTO CO., INC., Tokyo (JP)

(72) Inventors: Sergey Vasilievich Smirnov, Moscow (RU); Irina Lvovna Tokmakova, Moscow (RU)

(73) Assignee: AJINOMOTO CO., INC., Tokyo (JP)

( * ) Notice: Subject to any disclaimer, the term of this patent is extended or adjusted under 35 U.S.C. 154(b) by 846 days.

(21) Appl. No.: 17/132,270

(22) Filed: Dec. 23, 2020

(65) Prior Publication Data

US 2021/0115484 A1    Apr. 22, 2021

Related U.S. Application Data

(63) Continuation of application No. PCT/JP2019/028570, filed on Jul. 11, 2019.

(51) Int. Cl.
| | | |
|---|---|---|
| *C12P 19/26* | (2006.01) | |
| *C12N 9/10* | (2006.01) | |
| *C12N 9/16* | (2006.01) | |
| *C12N 15/52* | (2006.01) | |

(52) U.S. Cl.
CPC ............. *C12P 19/26* (2013.01); *C12N 9/13* (2013.01); *C12N 9/16* (2013.01); *C12N 15/52* (2013.01); *C12Y 208/02001* (2013.01); *C12Y 208/02008* (2013.01); *C12Y 301/03002* (2013.01); *C12Y 301/03007* (2013.01)

(58) Field of Classification Search
None
See application file for complete search history.

(56) References Cited

U.S. PATENT DOCUMENTS

| 6,232,093 B1 | 5/2001 | Van Houdenhoven et al. |
|---|---|---|
| 2019/0284590 A1 | 9/2019 | Jendresen et al. |

FOREIGN PATENT DOCUMENTS

| WO | WO2004/017910 A2 | 3/2004 |
|---|---|---|
| WO | WO2006/120425 A1 | 11/2006 |
| WO | WO2012/116048 A1 | 8/2012 |
| WO | WO2017/144671 A1 | 8/2017 |

OTHER PUBLICATIONS

Gallagher, J. T., et al., "Molecular distinctions between heparan sulphate and heparin. Analysis of sulphation patterns indicates that heparan sulphate and heparin are separate families of N-sulphated polysaccharides," Biochem. J. 1985;230(3):665-674.

PubChem CID: 772, PubChem database, National Center for Biotechnology Information (NCBI), https://pubchem.ncbi.hlm.nih.gov, Heparin, downloaded Aug. 14, 2020, pp. 1-51.

PubChem CID: 53477714, PubChem database, National Center for Biotechnology Information (NCBI), https://pubchem.ncbi.nlm.nih.gov, (2S,3R,4R,5S,6R)-4-Hydroxy-3-methoxy-6-{[(2S,3R,4S,5S,6R)-6-methoxy-4-oxido-5-[(sulfooxy)amino]-2-[(sulfooxy)methyl]oxan-3-yl]oxy}-5-(sulfooxy)oxane-2-carboxylate, downloaded Dec. 14, 2020, pp. 1-15.

Zhang, Z., et al., "Solution Structures of Chemoenzymatically Synthesized Heparin and Its Precursors," J. Am. Chem. Soc. 2008; 130(39):12998-13007.

Hatzios, S. K., et al., "The Mycobacterium tuberculosis CysQ phosphatase modulates the biosynthesis of sulfated glycolipids and bacterial growth," Bioorg. Med. Chem. Lett. 2011;21:4956-4959.

Kuberan, B., et al., "Chemoenzymatic Synthesis of Classical and Non-classical Anticoagulant Heparan Sulfate Polysaccharides," J. Biol. Chem. 2003;278(52):52613-52621.

Mulloy, B., et al., "Pharmacology of Heparin and Related Drugs," Pharmacol. Rev. 2015;68(1):76-141.

Shriver, Z., et al., "Heparin and Heparan Sulfate: Analyzing Structure and Microheterogeneity," HandB. Exp. Pharmacol. 2013;207:159-176.

Sugahara, K., et al., "Heparin and Heparan Sulfate Biosynthesis," IUBMB Life 2002;54(4):163-175.

Van Der Meer, J.-Y., et al., "From Farm to Pharma: An Overview of Industrial Heparin Manufacturing Methods," Molecules 2017;22(6):1025.

International Search Report and Written Opinion for PCT Patent App. No. PCT/JP2019/028570 (Nov. 12, 2019).

*Primary Examiner* — Michelle F. Paguio Frising
*Assistant Examiner* — Grant C Currens
(74) *Attorney, Agent, or Firm* — Cermak & McGowan LLP; Shelly Guest Cermak

(57) ABSTRACT

A method for enzymatic sulfurylation of a substrate is provided which includes the steps of reacting the substrate with 3'-phosphoadenosine-5'-phosphosulfate (PAPS) in a medium containing a bacterium belonging to the family Enterobacteriaceae to produce a sulfated derivative of the substrate, and collecting the sulfated derivative from the medium, wherein the bacterium has been modified to produce, at least, a protein having sulfotransferase activity, and to attenuate expression of an aphA gene, a cysQ gene, or a cpdB gene, or a combination of these.

17 Claims, 4 Drawing Sheets

Specification includes a Sequence Listing.

METHOD FOR ENZYMATIC SULFURYLATION OF ALCOHOLS AND AMINES USING BACTERIUM OF THE FAMILY ENTEROBACTERIACEAE

This application is a Continuation of, and claims priority under 35 U.S.C. § 120 to, International Application No. PCT/JP2019/028570, filed Jul. 11, 2019, and claims priority therethrough under 35 U.S.C. § 119 to Russian Patent Application No. 2018125379, filed Jul. 11, 2018, the entireties of which are incorporated by reference herein. Also, the Sequence Listing filed electronically herewith is hereby incorporated by reference (File name: 2020-12-23T_US-623_Seq_List; File size: 316 bytes; Date recorded: Dec. 23, 2020).

BACKGROUND INFORMATION

General Field

The present invention relates to the microbiological industry, and specifically to a method for enzymatic sulfurylation of alcohols and amines in a medium containing a bacterium belonging to the family Enterobacteriaceae for the production of O- and N-sulfated derivatives of the alcohols and amines. The method can be used to produce, for example, heparin and A heparan sulfate.

Description of the Related Art

A Inorganic and organic molecules containing one or more sulfate groups are known. Among them, biomolecules are known to exist that contain sulfate group(s), and which play an A important role in biological processes, and these include, for example, heparin, sulfate, chondroitin sulfate, choline sulfate, and dermatan sulfate. Heparin and heparan sulfate are of particular interest as they can be used in the pharmaceutical industry for, for example, therapeutic treatments.

Heparin and heparan sulfate (abbreviated as "HS") are linear polysaccharides having variably sulfated repeating disaccharide units. Heparin is produced primarily by mast cells of animals, whereas, HS is made by almost all types of cells. Heparin and HS can interact with numerous proteins and regulate various biological processes such as, for example, cell cycle, cell growth, cellular differentiation, cell adhesion, motility, lipid metabolism, angiogenesis, blood coagulation, abolishing detachment activity by GrB (Granzyme B), and tumor metastasis. The use of heparin to treat and prevent deep vein thrombosis, pulmonary embolism, and arterial thromboembolism is known. Heparin is also used in the treatment of heart attacks and unstable angina.

The chemical structure, that is, the type and number of basic polysaccharide components that make up molecules of heparin and HS, can vary depending on the tissue and the developmental stage. Therefore, there is no common heparin and HS structures. Nonetheless, the major structural motifs (–4GlcA1β-4GlcNAcα1-) and (–4)-α-L-IdoA2S-(1-4)-D-GlcNS6S-(1-) of repeating disaccharide units are present in the glycosylaminoglycan backbone of heparin and HS (Kuberan B. et al., Chemoenzymatic synthesis of classical and non-classical anticoagulant heparan sulfate polysaccharides, *J. Biol. Chem.*, 2003, 278(52):52613-52621; Mulloy B. et al., Pharmacology of heparin and related drugs, *Pharmacol. Rev.*, 2016, 68(1):76-141). The basic differences in molecular structures of heparin and HS are known, and these include molecular weight, sulfation ratio, and the content of iduronic acid (abbreviated as "IdoA") residues (see, for example, Gallagher J. T. and Walker A., Molecular distinctions between heparan sulphate and heparin. Analysis of sulphation patterns indicates that heparan sulphate and heparin are separate families of N-sulphated polysaccharides, *Biochem J.*, 1985, 230(3):665-674; Shriver Z. et al., Heparin and heparan sulfate: analyzing structure and microheterogeneity, *Handb. Exp. Pharmacol.*, 2012, 207:159-176). Furthermore, the anticoagulant activity of heparin is about 100 times higher as compared with the same activity of HS.

The biosynthesis of heparin and heparan sulfate from glucuronic acid (abbreviated as "GlcA") and N-acetylated glucose (abbreviated as "GlcNAc") units has been studied in detail (see, for example, Mulloy B. et al., 2016; Sugahara K. and Kitagawa H., Heparin and heparan sulfate biosynthesis, *IUBMB Life*, 2002, 54(4):163-175). In particular, biosynthetic events for modifying the glycosylaminoglycan backbone (so-called heparosan) to produce heparin and HS were described. The biosynthesis of heparin and HS includes the steps of i) N-deacetylation and N-sulfation of GlcNAc residues catalyzed by HS/heparin GlcNAc N-deacetylase/N-sulfotransferase (abbreviated as "NDNST"), ii) glucuronyl C5-epimerization catalyzed by heparosan-N-sulfate-glucuronate C5-epimerase (abbreviated as "HNSG-5epi", "C5-epi") that converts glucuronic acid (abbreviated as "GlcA") residues into IdoA residues, iii) consecutive 0-sulfation of hydroxyl groups located at the C2-position of IdoA residues, and C6- and C3-positions of N-sulfoglucosamine (abbreviated as "GlcNS) residues catalyzed, respectively, by heparan sulfate 2-O-sulfotransferase (abbreviated as "HS 2-OST"), heparan sulfate 6-O-sulfotransferase (abbreviated as "HS 6-OST"), and heparan sulfate 3-O-sulfotransferase (abbreviated as "HS 3-OST"). The N- and O-sulfation occurs in the presence of a donor of sulfo group 3'-phosphoadenosine 5'-phosphosulfate (abbreviated as "PAPS"). The ratio of sulfation can depend on the position and kind of the functional group to be sulfated (FIG. 1). Moreover, the biosynthetic events from heparosan to heparin and HS are not uniform, and they can result in a diverse range of chemical structures. An example of a chemical structure of heparin is shown in FIG. 2A (PubChem CID: 772, PubChem database, National Center for Biotechnology Information (NCBI), pubchem.ncbi.nlm.nih.gov), and an example of a chemical structure of HS is shown in FIG. 2B (PubChem CID: 53477714).

Methods for manufacturing heparin and HS are known, and these include, for example, isolation and purification of heparin from mammalian and non-mammalian sources, chemical, chemoenzymatic, and biotechnological techniques. An industrial process for the isolation of heparin from animals was started in 1922, and it is still considered as the major method for producing heparin. Porcine, bovine, canine, and sheep (ovine) can be used as the source of heparin (van der Meer J. Y. et al., From farm to pharma: an overview of industrial heparin manufacturing methods, *Molecules*, 2017, 22(6):1025). However, there are religious and health concerns when heparin isolated from a mammalian source is used. These problems were somewhat solved by using dromedary (*Camelus* dromedaries) as the heparin source. Despite that heparin isolated from animal sources has undesirable side-effects such as, for example, bleeding and heparin-induced thrombocytopenia (HIT) with arterial thrombosis, it is still in use for combination therapy to treat humans after strokes and heart attacks.

Methods for producing heparin by isolating it from poultry such as, for example, chicken and turkey; fish such as, for example, salmon (Salmo salar); and other sources, are also known (van der Meer J. Y. et al, 2017, and the references therein). Patent documents that disclose the methods for the production of heparin from animal and marine sources have been published. For example, a simplified process for the extraction of heparin from animal mucosa tissue using an enzymatic hydrolysis step of the raw material at ambient temperature is known (U.S. Pat. No. 6,232,093 B1). In another method, a very low molecular weight heparin (abbreviated as "VLMWH") was isolated from fish sources using chromatography techniques (WO2006120425 A1).

As the heparin and heparan sulfate (HS) at the biosafety level are of therapeutic importance, methods for inexpensive and large-scale commercial production of such substances from non-animal sources are in demand. Therefore, alternative methods for producing heparin and HS have been developed. For example, it was shown that HS can rapidly and easily be synthesized using a set of cloned enzymes involved in biosynthesis of HS (Kuberan B. et al., 2003). However, this method is laborious and expensive as it requires purified human glucuronyl C5-epimerase and heparan sulfate 2-, 3- and 6-O-sulfotransferases, and PAPS as a donor of sulfo group. In another example, the bioengineered heparin was obtained from heparosan using a chemoenzymatic approach including the steps of treating heparosan with i) aqueous solution of alkali to attain a single-step partial depolymerisation of heparosan and N-deacetylation of amino groups, ii) trimethylamine-sulfur trioxide complex to perform selective N-sulfation, iii) a mixture of C5-epimerase and 2-O-sulfotransferase to attain isomerization of the carboxyl group at the C5-atom of the GlcA residues and 2-O-sulfation of the IdoA residues, iv) a mixture of 6-O-sulfotransferases to attain 6-O-sulfation of the GlcNS residues, and v) a 3-O-sulfotransferase to attain 3-O-sulfation of the GlcNS(6S) residues (WO2012116048 A1). The bioengineered heparin produced by the method was substantially equivalent to the pharmaceutical heparin with reference to the content of N-acetylglucosamine and N-sulfoglucosamine, number average molecular weight ($M_N$), weight average molecular weight (Mw), and polydispersity index (PDI). In the described method, a regeneration system was used to restore a donor of sulfo group (PAPS) due to its very high cost (Zhang Z. et al., Solution structures of chemoenzymatically synthesized heparin and its precursors, *J. Am. Chem. Soc.*, 2008, 130(39):12998-13007).

However, a method for enzymatic sulfurylation of a substrate to produce its sulfated derivative by reacting the substrate with a donor of sulfo group in a medium containing a bacterium belonging to the family Enterobacteriaceae, which has been modified to produce, at least, a protein having sulfotransferase activity and attenuate the expression of an aphA gene, a cysQ gene or a cpdB gene, or a combination of these, is not known.

SUMMARY

According to the presently disclosed subject matter, a novel method for enzymatic sulfurylation of a substrate having, at least, one hydroxyl group or, at least, one amino group to produce a sulfated derivative thereof such as, respectively, an O-sulfated derivative or an N-sulfated derivative of the substrate is provided herein. In an exemplary embodiment of the method as described herein, a heparosan N-sulfate can be sulfurylated to produce an O-sulfated A derivative thereof such as, for example, heparin and heparan sulfate having, at least, one additional O-sulfo group as compared with the initial heparosan N-sulfate. Therefore, according to the presently disclosed subject matter, 0-sulfated derivatives of heparosan N-sulfate can be produced not using animal sources.

The method as described herein can include the steps of reacting a substrate with a donor of sulfo group which can be, for example, 3'-phosphoadenosine-5'-phosphosulfate (PAPS) in a medium containing a bacterium belonging to the family Enterobacteriaceae, which has been modified to produce, at least, a protein having sulfotransferase activity and to attenuate expression of an aphA gene, a cysQ gene and a cpdB gene, or a combination of these. An advantage of the method is that a crude lysate of cells of the bacterium contains a protein having the desired activity such as, for example, a protein having sulfotransferase activity, and hence the crude lysate can be successfully used in the method as described herein. That is, in the method as described herein, one or more proteins having the desired activities may be used without prior isolation and/or purification. Therefore, a process for sulfurylation of alcohols and amines can be simplified and the cost of the process can be reduced when the method as described herein is used.

The method can be improved further by modifying the bacterium that can be used in the method as described herein such that the bacterium can produce also a protein having 3'-phosphoadenosine-5'-phosphosulfate-sulfotransferase activity so that costly and unstable PAPS can easily be regenerated and re-used in the method. Alternatively, the method can be improved further by using the medium that can be used in the method as described herein such that the medium contains the bacterium as described herein and a protein having 3'-phosphoadenosine-5'-phosphosulfate-sulfotransferase activity so that PAPS can be regenerated in the medium. Therefore, according to the presently disclosed subject matter, O- and N-sulfated derivatives of the substrate can be produced with high yield at a much lower price.

It is one aspect of the present invention to provide a method for enzymatic sulfurylation of a substrate comprising: (i) reacting the substrate with 3'-phosphoadenosine-5'-phosphosulfate in a medium containing a bacterium belonging to the family Enterobacteriaceae to produce a sulfated derivative of said substrate, and (ii) collecting the sulfated derivative from the medium, wherein said bacterium has been modified: (A) to produce, at least, a protein having sulfotransferase activity, and (B) to attenuate expression of an aphA gene or a cysQ gene.

It is another aspect of the invention to provide the method as described above, wherein said bacterium modified to attenuate expression of the aphA gene has been modified further to attenuate expression of the cysQ gene or a cpdB gene, or a combination thereof.

It is another aspect of the invention to provide the method as described above, wherein said bacterium modified to attenuate expression of the cysQ gene has been modified further to attenuate expression of the aphA gene or the cpdB gene, or a combination thereof.

It is another aspect of the invention to provide the method as described above, wherein said protein having sulfotransferase activity is selected from the group consisting of a protein having O-sulfotransferase activity, a protein having N-sulfotransferase activity, and a protein having N-deacetylase/N-sulfotransferase activity.

It is another aspect of the invention to provide the method as described above, wherein said protein having O-sulfotransferase activity is selected from the group consisting of a protein having heparan sulfate 2-O-sulfotransferase activity, a protein having heparan sulfate 3-O-sulfotransferase activity, a protein having heparan sulfate 6-O-sulfotransferase activity, and a combination thereof.

It is another aspect of the invention to provide the method as described above, wherein said bacterium has been modified further to produce a protein having heparosan-N-sulfate-glucouronate 5-epimerase activity.

It is another aspect of the invention to provide the method as described above, wherein said bacterium has been modified further to produce a protein having 3'-phosphoadenosine-5'-phosphosulfate-sulfotransferase activity.

It is another aspect of the invention to provide the method as described above, wherein said medium contains the protein having 3'-phosphoadenosine-5'-phosphosulfate-sulfotransferase activity.

It is another aspect of the invention to provide the method as described above, wherein said substrate has, at least, one chemical group selected from a hydroxyl group and an amino group.

It is another aspect of the invention to provide the method as described above, wherein said substrate is selected from the group consisting of heparosan, heparan sulfate, and heparin.

It is another aspect of the invention to provide the method as described above, wherein said sulfated derivative is selected from the group consisting of heparin, heparan sulfate, chondroitin sulfate, choline sulfate, and dermatan sulfate.

It is another aspect of the invention to provide the method as described above, wherein said bacterium belongs to the genus *Escherichia* or *Pantoea*.

It is another aspect of the invention to provide the method as described above, wherein said bacterium is *Escherichia coli* or *Pantoea ananatis*.

It is another aspect of the present invention to provide a method for producing a sulfated derivative of a substrate comprising: (i) reacting the substrate with 3'-phosphoadenosine-5'-phosphosulfate in a medium containing a bacterium belonging to the family Enterobacteriaceae to produce the sulfated derivative of said substrate, and (ii) collecting the sulfated derivative from the medium, wherein said bacterium has been modified: (A) to produce, at least, a protein having sulfotransferase activity, and (B) to attenuate expression of an aphA gene or a cysQ gene.

It is another aspect of the invention to provide the method as described above, wherein said bacterium modified to attenuate expression of the aphA gene has been modified further to attenuate expression of the cysQ gene or a cpdB gene, or a combination thereof.

It is another aspect of the invention to provide the method as described above, wherein said bacterium modified to attenuate expression of the cysQ gene has been modified further to attenuate expression of the aphA gene or the cpdB gene, or a combination thereof.

Still other objects, features, equivalents, and attendant advantages of the present invention will become apparent to those skilled in the art from a reading of the following detailed description of embodiments constructed in accordance therewith, taken in conjunction with the accompanying figures.

The invention of the present application will now be described in more detail with reference to the exemplary embodiments, given only by way of example, and with reference to the accompanying figures.

DETAILED DESCRIPTION

1. Bacterium

Figure 1:
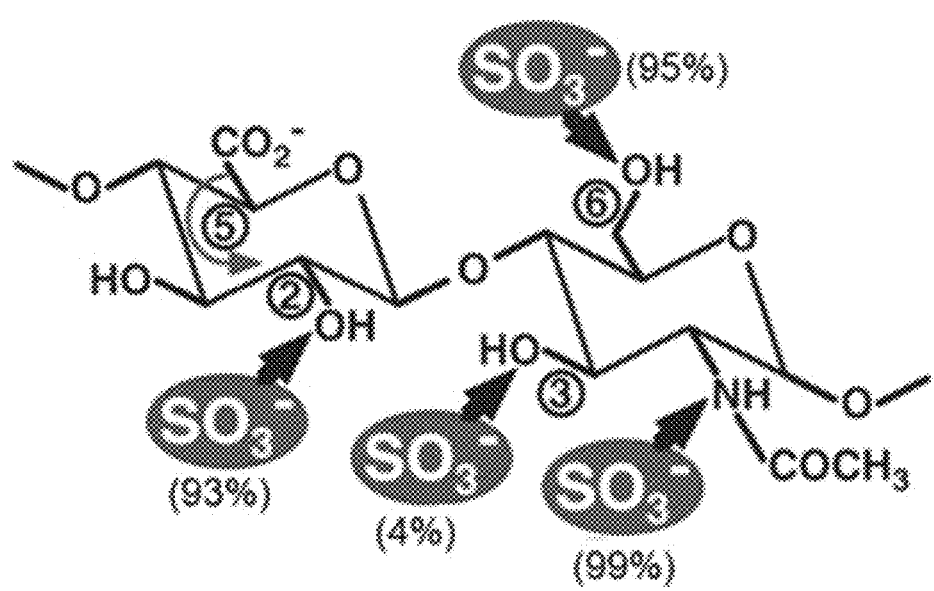
FIG. 1 shows the sulfation ratio of hydroxyl groups and amino group of a glycosylaminoglycan unit having the (-4GlcA1β-4GlcNAcα1-) structure using N- and O-sulfotransferases. The sulfation ratio (in %) is shown in parenthesis, and the positions of hydroxyl groups susceptible to the sulfation are shown in circles. The isomerization of carboxyl group at the C5-position of the glucuronic acid (GlcA) residue is shown by the curved arrow.
Figure 2A:
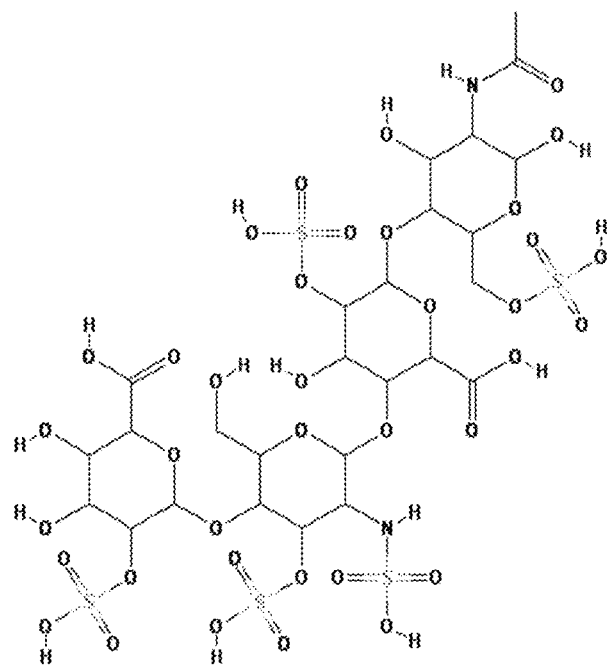
FIG. 2A shows the exemplary chemical structure of a heparin.
Figure 2B:
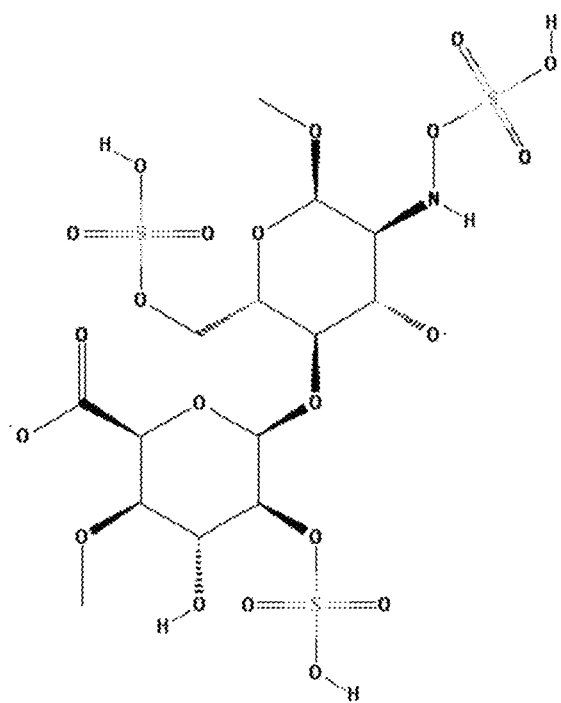
FIG. 2B shows the exemplary chemical structure of a heparan sulfate.

The bacterium that can be used in the method as described herein can be a bacterium belonging to the family Enterobacteriaceae that has been modified to produce, at least, a protein having sulfotransferase activity. The bacterium may be modified further to produce a protein having heparosan-N-sulfate-glucouronate 5-epimerase activity and/or a protein having 3'-phosphoadenosine-5'-phosphosulfate-sulfotransferase activity. The bacterium that can be used in the method as described herein has also been modified to attenuate expression of an aphA gene, a cysQ gene or a cpdB gene, or a combination of these.

In the method as described herein, a bacterium belonging to the family Enterobacteriaceae can be from the genera *Enterobacter, Erwinia, Escherichia, Klebsiella, Morganella, Pantoea, Photorhabdus, Providencia, Salmonella, Yersinia*, and so forth, so long as the bacterium can be able to produce, at least, a protein having sulfotransferase activity and can be modified to attenuate expression of, at least, one gene selected from the aphA gene, the cysQ gene, and the cpdB gene, or a combination of them. Specifically, those classified into the family Enterobacteriaceae according to the taxonomy used in the NCBI (National Center for Biotechnology Information) database (ncbi.nlm.nih.gov) can be used. Examples of strains from the family Enterobacteriaceae which can be modified include a bacterium of the genus *Escherichia, Enterobacter* or *Pantoea*.

Strains of *Escherichia* bacterium which can be modified to obtain *Escherichia* bacteria in accordance with the presently disclosed subject matter are not particularly limited, and specifically, those described in the work of Neidhardt et al. can be used (Bachmann, B. J., Derivations and genotypes of some mutant derivatives of *Escherichia coli* K-12, p. 2460-2488. In F. C. Neidhardt et al. (ed.), *Escherichia coli* and *Salmonella*: cellular and molecular biology, 2$^{nd}$ ed. ASM Press, Washington, D.C., 1996). The species *Escherichia coli* (*E. coli*) is a particular example. Specific examples of *E. coli* include *E. coli* W3110 (ATCC 27325), *E. coli* MG1655 (ATCC 47076), and so forth, which are derived from the prototype wild-type strain, *E. coli* K-12 strain.

These strains are available from, for example, the American Type Culture Collection (ATCC; Address: P.O. Box 1549, Manassas, VA 20108, United States of America). That is, registration numbers are assigned to the respective strains, and the strains can be ordered by using these registration numbers (refer to atcc.org). The registration numbers of the strains are listed in the catalogue of the American Type Culture Collection.

Examples of the *Enterobacter* bacteria include *Enterobacter agglomerans, Enterobacter aerogenes*, and so forth. Examples of the *Pantoea* bacteria include *Pantoea ananatis* (*P. ananatis*), and so forth. Some strains of *Enterobacter agglomerans* were recently reclassified into *Pantoea agglomerans, Pantoea ananatis* or *Pantoea stewartii* on the basis of nucleotide sequence analysis of 16S rRNA, etc. A bacterium belonging to either genus *Enterobacter* or *Pantoea* may be used so long as it is a bacterium classified into the family Enterobacteriaceae. When a *P. ananatis* strain is bred by genetic engineering techniques, *P. ananatis* AJ13355 strain (FERM BP-6614), AJ13356 strain (FERM BP-6615), AJ13601 strain (FERM BP-7207) and derivatives thereof can be used. These strains were identified as *Enterobacter agglomerans* when they were isolated, and deposited as *Enterobacter agglomerans*. However, they were recently re-classified as *P. ananatis* on the basis of nucleotide sequencing of 16S rRNA and so forth as described above.

The bacterium that can be used in the method as described herein refers to a bacterium in which activity of a protein having the desired activity can be determined. For example, a bacterium which can be modified to produce a protein having sulfotransferase activity can refer to the bacterium in which the activity of the protein having sulfotransferase activity can be determined. The explanations given herein to "a bacterium which can be modified to produce a protein having sulfotransferase activity" can also be similarly applied to any bacterium that can be used in the method as described herein, in particular, a bacterium which can be modified to produce a protein having the desired activity such as, for example, "a bacterium which can be modified to produce a protein having heparosan-N-sulfate-glucouronate 5-epimerase activity" and "a bacterium which can be modified to produce a protein having 3'-phosphoadenosine-5'-phosphosulfate-sulfotransferase activity".

The phrase "a protein having sulfotransferase activity" can mean the protein that causes catalysis of the reaction of the transfer of a sulfo group (—$SO_3H$) from a donor molecule (also referred to as a donor of sulfo group) to a substrate, which can be an alcohol, an amine or an amino alcohol, in a process called sulfurylation that can also be referred to as sulfation or sulfonation (the Enzyme Commission (EC) number: 2.8.2.-; Chapman E. et al., Sulfotransferases: structure, mechanism, biological activity, inhibition, and synthetic utility; *Angew. Chem. Int. Ed. Engl.*, 2004, 43(27):3526-3548). A protein having sulfotransferase activity can be referred to as sulfotransferase (abbreviated as "ST"). As the sulfotransferase that can be used in the method as described herein may be an O-sulfotransferase or an N-sulfotransferase as it will be explained below, the phrase "a protein having sulfotransferase activity" can include phrases "a protein having O-sulfotransferase activity" and "a protein having N-sulfotransferase activity". Therefore, the phrase "a protein having O-sulfotransferase activity" can mean a protein that causes catalysis of the reaction of the transfer of a sulfo group from a donor molecule to a substrate, which can be an alcohol or an amino alcohol, in O-sulfurylation process; and the phrase "a protein having N-sulfotransferase activity" can mean a protein that causes catalysis of the reaction of the transfer of a sulfo group from a donor molecule to a substrate, which can be an amine or an amino alcohol, in N-sulfurylation process. The O-sulfurylation and N-sulfurylation with reference to a process can collectively be referred to as sulfurylation process.

The sulfotransferases that are able to sulfurylate hydroxyl groups of substrates to produce sulfated derivatives thereof can be collectively referred to as O-sulfotransferases (abbreviated as "O-ST"s, or "OST"s). Specifically, O-sulfotransferases are enzymes that can cause catalysis of the reaction of the transfer of sulfo group to a hydroxyl group (—OH) of the substrate to produce a sulfated derivative thereof, which is also called sulfate, having the chemical formula of R—$OSO_3H$ or R—$OSO_3^-$, wherein "R" can refer to a chemical group such as, for example, an organic group that is well-known to the person of ordinary skill in the art. The sulfotransferases that are able to sulfurylate amino groups of substrates to produce sulfated derivatives thereof can be collectively referred to as N-sulfotransferases (abbreviated as "N-ST"s, or "NST"s). Specifically, N-sulfotransferases are enzymes that can cause catalysis of the reaction of the transfer of sulfo group to a primary and/or secondary amino group (—$NH_2$, —NHR') of the substrate to produce a sulfated derivative thereof, which is also called sulfamate, having the chemical formula of R—NH—$SO_3H$ or R—NH—$SO_3^-$, and/or R—NR'—$SO_3H$ or R—NR'—$SO_3$—, wherein R and R' refer to the chemical group R as described above, and wherein R and R' may refer to chemical groups of the same or different kinds.

OSTs and NSTs of various kinds are known, and these include, but are not limited to, aryl sulfotransferase (EC 2.8.2.1), alcohol sulfotransferase (EC 2.8.2.2), amine sulfotransferase (EC 2.8.2.3), [heparan sulfate]-glucosamine N-sulfotransferase (EC 2.8.2.8, abbreviated as "N-HSST"), chondroitin 6-sulfotransferase (EC 2.8.2.17), keratan sulfotransferase (2.8.2.21), [heparan sulfate]-glucosamine 3-sulfotransferase isoforms 1, 2 and 3 (accordingly, EC 2.8.2.23, 2.8.2.29, and 2.8.2.30; abbreviated as "3-OST-1", "3-OST-2", and "3-OST-3"), and so forth, which are classified, for example, in the UniProtKB Database (enzyme.expasy.org).

Sulfotransferases native to various organisms such as, for examples, mammals, including human, fishes, insects, worms, and so forth are known, and these may be used in the method as described herein. Specific examples of OST include, but are not limited to, heparan sulfate 2-O-sulfotransferase (HS 2-OST), heparan sulfate 3-O-sulfotransferase (HS 3-OST), and heparan sulfate 6-O-sulfotransferase (HS 3-OST) that are capable of O-sulfurylating (alternatively, O-sulfating, O-sulfonating) hydroxyl groups located, respectively, at the C2-position of hexuronic acid residues (particularly, L-iduronic acid (IdoA) residues), and C3- and C6-positions of the N-sulfoglucosamine (GlcNS) residues in heparan N-sulfate.

For example, HS 2-OST native to human (*Homo sapiens*; UniProtKB Database, entry No. Q7LGA3), mouse (*Mus musculus*; entry No. Q8R3H7), chicken (*Gallus gallus*; entry No. Q76KB1), a frog (for example, *Xenopus laevis*; entry No. 093336), zebrafish (*Danio rerio*; entry No. Δ1L1P8), a roundworm (for example, Trichinella pseudospiralis; entry No. Δ0Δ0V1JLD7), an insect (for example, *Lygus hesperus*; entry No. Δ0Δ146LU86), and so forth can be used.

In another example, HS 3-OST native to human (*Homo sapiens*; UniProtKB Database, entry No. Q9Y663), mouse (*Mus musculus*; entry No. 035310), rat (*Rattus norvegicus*; entry No. Q80W66), a fruit fly (*Drosophila melanogaster*; entry No. Q9VWJ7), hydra (*Hydra vulgaris, Hydra attenu-*

*ata*; entry No. T2MJ19), a nematode (for example, *Trichinella murrelli*; entry No. A0A0V0UDE4), and so forth can be used.

In another example, HS 6-OST native to human (*Homo sapiens*; UniProtKB Database, entry No. O60243), mouse (*Mus musculus*; entry No. Q9QYK5), chicken (*Gallus gallus*; entry No. Q76KB2), bovine (*Bos taurus*; entry No. 1BNW3), a monkey (for example, *Rhesus macaque* (*Macaca mulatta*); entry No. F7DP42), a bat (*Myotis lucifugus*; entry No. G1PY33), a fruit fly (*Drosophila persimilis*; entry No. B4GL90), a nematode (for example, *Caenorhabditis briggsae*; entry No. A8XKD5), and so forth can be used.

Specific examples of NST include, but are not limited to, amine sulfotransferases and arylamine sulfotransferases that are capable of N-sulfurylating (alternatively, N-sulfating, N-sulfonating) primary and secondary amino groups of amino group-containing substrates such as, for example, aniline, phenylamine, benzenamine, arylamine, 2-naphthylamine, and the like. For example, NST native to *Daphnia magna* (UniProtKB Database, entry No. A0A0P5VC43), a fruit fly (for example, *Zeugodacus cucurbitae*; entry No. A0A0A1X0U6), those listed in, for example, the KEGG (Kyoto Encyclopedia of Genes and Genomes) Database (genome.jp), and so forth can be used.

It is known that a protein having N-sulfotransferase activity may have, in addition to that property, N-deacetylation activity. Therefore, in the particular cases, a protein having N-sulfotransferase activity can also be referred to as a protein having N-deacetylase/N-sulfotransferase activity, and it also can be used in the method as described herein. The phrase "a protein having N-deacetylase/N-sulfotransferase activity" can mean the protein that causes catalysis of the reaction of the N-deacetylation and the N-sulfation of glucosamine (GlcNAc) residues of the glycosaminoglycan in heparan sulfate (heparan sulfate N-deacetylase, EC 3.-.-.-; heparan sulfate N-sulfotransferase, EC 2.8.2.-). The protein having N-deacetylase/N-sulfotransferase activity can be referred to as bifunctional N-deacetylase/N-sulfotransferase (abbreviated as "NDST").

Specific examples of NDST include, but are not limited to, the NDST native to human (*Homo sapiens*; UniProtKB Database, entry No. P52848), mouse (*Mus musculus*; entry No. Q3UHN9), pig (*Sus scrofa*; entry No. F6XY50), sheep (*Ovis aries*; entry No. UPI00072F9665), horse (*Equus caballus*; entry No. F6SHQ3), a bird (for example, sunbittern (*Eurypyga helias*); entry No. UPI0005288C4A), and so forth, and these proteins can be used in the method as described herein.

The activity a protein having sulfotransferase activity can be determined by radioisotopic method using [$^{35}$S] 3'-phosphoadenosine-5'-phosphosulfate and scintillation counting (Habuchi H. et al., Biosynthesis of heparan sulphate with diverse structures and functions: two alternatively spliced forms of human heparan sulphate 6-O-sulphotransferase-2 having different expression patterns and properties, Biochem. J., 2003, 371(Pt 1):131-142) or a coupled bienzymic colorimetric assay using an aryl sulfotransferase and p-nitrophenylsulfate (abbreviated as "pNPS") as a donor of sulfo group (Sterner E. et al., Assays for determining heparan sulfate and heparin O-sulfotransferase activity and specificity, Anal. Bioanal. Chem., 2014, 406(2):525-536). The protein concentration can be determined by the Bradford protein assay or the method of Lowry using bovine serum albumin (BSA) as a standard and a Coomassie dye (Bradford M. M., Anal. Biochem., 1976, 72:248-254; Lowry O. H. et al., J. Biol. Chem., 1951, 193:265-275).

The substrate which can be used in the method as described herein can be any substrate (that is, any molecule) having, at least, one hydroxyl group or, at least, one amino group, or a combination of these, so long as the substrate can be sulfurylated using an OST or an NST, or a combination of these, to produce a sulfated derivative of the substrate. It is also acceptable that the substrate can have, alone or in addition to one or more hydroxyl groups and/or one or more amino groups, at least, one amino group that is N-acetylated, so long as the substrate can be sulfurylated using an NDST. The substrates can be, but are not limited to, those that are described in, for example, Chapman E. et al., 2004, and these include phenols, including 4-nitrophenol (also known as p-nitrophenol, abbreviated as "pNP"), catecholamines, aryl hydroxylamines, hydroxysteroids, dopamine, tyramine, minoxidol, pregnenolone, dehydroepiandrosterone (abbreviated as "DHEA"), an oligosaccharide such as, for example, a heparosan, a sulfated derivative of heparosan such as, for example, a heparan sulfate having N-acetylated glucosamine (GlcNAc) residues, a heparan sulfate glycosaminoglycan (abbreviated as "HSGAG"), N-sulfated heparosan (abbreviated as "NS-heparosan"), keratan sulfate, and so forth. Heparosan is a particular example of the substrate, the methods for producing of which are known (see, for example, US 2016201103 A1).

As a sulfo group donor which can be used in the method as described herein, any molecule can be used so long as the molecule can donate sulfo group to a sulfotransferase such that sulfotransferase activity of the sulfotransferase can be determined. Virtually, any molecule that can donate a sulfo group to O-sulfotransferase, N-sulfotransferase, and/or N-deacetylase/N-sulfotransferase so that said sulfotransferase(s) can be the protein(s) having sulfotransferase activity, can be used. For example, 3'-phosphoadenosine 5'-phosphosulfate (PAPS; PubChem CID: 10214), also known as 3'-phospho-5'-adenylyl sulfate, or a salt thereof such as, for example, a sodium or lithium salt can serve as a donor of sulfo group (see, for example, Scheme 1 in Chapman E. et al., 2004). The PAPS may be used exogenously, that is, it can be added into a medium containing the bacterium that can be used in the method as described herein; and/or it may be used in an endogenous form natively bound to sulfotransferase, because it is known that there are enzymes (ATP sulfurylase and adenosine 5'-phosphosulfate kinase) that catalyze the formation of PAPS in organisms which is then recruited by and bound to the sulfotransferase as a cofactor. As PAPS is an expensive and unstable chemical compound, it is preferable to use the PAPS that is synthesized endogenously by an organism and, thus, which is natively bound to sulfotransferase. In this case, a system for regenerating, or recycling PAPS in the medium, in which sulfurylation takes place, was developed (see, for example, FIG. 1 in Sterner E. et al., 2014; Gregory J. D. and Lipmann F., The transfer of sulfate among phenolic compounds with 3',5'-diphosphoadenosine as coenzyme, J. Biol. Chem., 1957, 229(2):1081-1090). In the system, a sulfotransferase converts PAPS to 3'-phosphoadenosine-5'-phosphate (abbreviated as "PAP") and sulfurylates a substrate. PAP is then recycled to PAPS using a protein having 3'-phosphoadenosine-5'-phosphosulfate-sulfotransferase activity that can utilize p-nitrophenylsulfate (pNPS) as the sulfo group donor for the PAP.

The phrase "a protein having heparosan-N-sulfate-glucouronate 5-epimerase activity" can mean the protein that causes catalysis of the reaction of the converting of D-glucuronic acid (GlcA) residues adjacent to N-sulfate sugar residues in N-sulfated heparosan to iduronic acid (IdoA) residues (EC 5.1.3.17; Mochizuki H. et al., Heparosanglucuronate 5-epimerase: Molecular cloning and characterization of a novel enzyme, *Glycobiology*, 2015, 25(7):735-744). The activity a protein having heparosan-N-sulfate-glucouronate 5-epimerase activity can be determined by radioisotopic methods using [5-$^3$H]heparosan as the substrate (Mochizuki H. et al., 2015).

The protein having heparosan-N-sulfate-glucouronate 5-epimerase activity can be referred to as heparosan-N-sulfate-glucouronate 5-epimerase (HNSG-5epi). Specific examples of HNSG-5epi include, but are not limited to, the HNSG-5epi native to human (*Homo sapiens*; UniProtKB Database, entry No. O94923), mouse (*Mus musculus*; entry No. Q9EPS3), bovine (*Bos taurus*; entry No. O18756), zebrafish (*Danio rerio*; entry No. Q6TS33), a hamster (for example, *Cricetulus griseus*; entry No. A0A061I8R4), sheep (*Ovis aries*; entry No. W5QB79), an elephant (for example, *Loxodonta africana*; entry No. G3T4X0), and so forth, and these proteins can be used in the method as described herein.

As pNPS can be used as a donor of sulfo group in the system for the regenerating PAPS, the phrase "a protein having 3'-phosphoadenosine-5'-phosphosulfate-sulfotransferase activity" with reference to a protein having such activity that can be used in the method as described herein can mean, in a broader sense, a protein having aryl sulfotransferase activity (EC 2.8.2.1), which is an example of a protein having O-sulfotransferase activity (EC 2.8.2.-). It would be, therefore, apparent to the person of ordinary skill in the art that the explanations given herein to a protein having O-sulfotransferase activity can also be similarly applied to a protein having aryl sulfotransferase activity, which, in turn, can be similarly applied to a protein having 3'-phosphoadenosine-5'-phosphosulfate-sulfotransferase activity. It is apparent now that activity of a protein having 3'-phosphoadenosine-5'-phosphosulfate-sulfotransferase activity can be determined using the methods that can be used for the determining the activity of a protein having sulfotransferase activity, and these methods include, for example, the method in which PAP as a substrate and pNPS as a donor of sulfo group are used (Sterner E. et al., 2014).

A protein having 3'-phosphoadenosine-5'-phosphosulfate-sulfotransferase activity can be referred to as 3'-phosphoadenosine-5'-phosphosulfate-sulfotransferase (abbreviated as "PAPS ST"), and it can mean, in a broader sense, aryl sulfotransferase. Specific examples of aryl sulfotransferase that can be used for the regenerating PAPS include, but are not limited to, the aryl sulfotransferase native to human (*Homo sapiens*; ST1A3, UniProtKB Database, entry No. PODMM9), rat (*Rattus norvegicus*; ST1A1, entry No. P17988; NCBI (The National Center for Biotechnology Information, ncbi.nlm.nih.gov) gene entry No. NP_114022.1), mouse (*Mus musculus*; ST1A1, entry No. P52840), and so forth.

It is known that an OST, NST, NDST, HNSG-5epi, and PAPS ST, may exist in different protein isoforms, which are a result of alternative splicing of the genes encoding the OST, NST, NDST, HNSG-5epi, and PAPS ST, and these protein isoforms may also be used in the method as described herein so long as they can be the proteins having the desired activities according to the method as explained herein.

The phrase "native to" with reference to a protein or a nucleic acid native to a particular species such as, for example, a bacterial or mammalian species can refer to a protein or a nucleic acid that is native to that species. That is, a protein or a nucleic acid native to a particular species can mean the protein or the nucleic acid, respectively, that exists naturally in the species and can be isolated from that species and sequenced using means known to the one of ordinary skill in the art. Moreover, as the amino acid sequence or the nucleotide sequence of a protein or nucleic acid, respectively, isolated from the species in which the protein or nucleic acid exists, can easy be determined, the phrase "native to" in reference to a protein or a nucleic acid can also refer to a protein or a nucleic acid that can be obtained using, for example, a genetic engineering technique, including recombinant DNA technology, or a chemical synthesis method, or the like, so long as the amino acid sequence of the protein or the nucleotide sequence of the nucleic acid thus obtained is identical, accordingly, to the amino acid sequence of the protein or the nucleotide sequence of the nucleic acid that exists naturally in the species. Examples of amino acid sequences native to particular species include, but are not limited to, peptides, oligopeptides, polypeptides, including proteins, specifically enzymes, and so forth. Examples of nucleotide sequences native to particular species include deoxyribonucleic acid (DNA) and ribonucleic acid (RNA), and these are not limited to regulatory sequences, including promoters, attenuators, terminators, and the like, genes, intergenic sequences, sequences encoding signal peptides, pro-moieties of proteins, artificial amino acid sequences, and so forth. Examples of amino acid sequences and nucleotide sequences, and homologues thereof native to various species are described herein, and these examples include, but are not limited to, heparan sulfate 2-O-sulfotransferase (HS 2-OST) native to long-tailed dwarf hamster (*Cricetulus longicaudatus*; UniProtKB, accession No. O0889.1), and encoded by the corresponding mRNA (GeneBank, accession No. D88811.1); heparosan-N-sulfate-glucouronate 5-epimerase (HNSG-5epi) native to zebrafish (*Danio rerio*; NCBI Reference Sequence, accession No. NP_998014.1), and encoded by the corresponding mRNA (NCBI Reference Sequence, accession No. NM_212849.1); aryl sulfotransferase 1A1 having the amino acid native to rat (*Rattus norvegicus*; NCBI Reference Sequence, NP_114022.1), and encoded by the corresponding mRNA (NCBI Reference Sequence, accession No. NM_031834.1).

The explanations given below to a protein having sulfotransferase activity with reference to the methods of modifying a bacterium with that protein, wherein the bacterium can be used in the method as described herein, can also be applied mutatis mutandis to any protein having the desired activity and that can be used in the method. Examples of a protein having the desired activity include, but are not limited to, a protein having heparosan-N-sulfate-glucouronate 5-epimerase activity and a protein having 3'-phosphoadenosine-5'-phosphosulfate-sulfotransferase activity, and so forth, because the bacterium may have other properties apart from those that are described herein.

The bacterium that can be used in the method as described herein has been modified to produce a protein having sulfotransferase activity. As a protein is encoded by a gene, it becomes apparent to the person of the ordinary skill in the art that the bacterium can be modified to express a gene that encodes a protein having sulfotransferase activity.

The phrase "a bacterium modified to express a gene that encodes a protein having sulfotransferase activity" can mean that the bacterium natively or naturally not having a gene that encodes a protein having sulfotransferase activity has been modified such that the bacterium contains the gene that encodes a protein having sulfotransferase activity (referred to as a host bacterium), wherein the gene is present natively or naturally in or native to an organism that is different from the host bacterium (referred to as a donor organism). The gene that is native to a donor organism and is introduced into a host bacterium can be referred to as a heterologous gene with reference to the host bacterium, for which said gene is not native or natural.

The phrase "a bacterium modified to express a gene that encodes a protein having sulfotransferase activity" also can mean that the host bacterium that has been introduced with the gene that encodes a protein having sulfotransferase activity became able to produce the protein having sulfotransferase activity as a result of such modification.

The bacterium that has been modified to produce a protein having sulfotransferase activity can be obtained by introducing a gene that encodes a protein having sulfotransferase activity. Methods for introducing a recombinant DNA into a recipient bacterium can be the conventional methods that have been reported and are well-known to the person of ordinary skill in the art. Such methods include, for example, transformation, transfection, infection, conjugation, and mobilization. Transformation, transfection, infection, conjugation or mobilization of a bacterium with the recombinant DNA containing a gene that encodes a protein having sulfotransferase activity can impart the bacterium an ability to express the gene and synthesize the protein encoded by the gene. For example, a method of treating recipient cells with calcium chloride so as to increase permeability of the cells of Escherichia coli K-12 to DNA has been reported for efficient DNA transformation and transfection (Mandel M. and Higa A., Calcium-dependent bacteriophage DNA infection, J. Mol. Biol., 1970, 53:159-162). Methods of specialized and/or generalized transduction are described (Morse M. L. et al., Transduction in Escherichia coli K-12, Genetics, 1956, 41(1):142-156; Miller J. H., Experiments in Molecular Genetics. Cold Spring Harbor, N.Y.: Cold Spring Harbor Lab. Press, 1972). Other methods for the random and/or targeted integration of DNA into the genome of a recipient organism can be applied such as, for example, «Mu-driven integration/amplification» (see, for example, Akhverdyan V. Z. et al., Appl. Microbiol. Biotechnol., 2011, 91:857-871), «Red/ET-driven integration» or «Red/ET-mediated integration» (Datsenko K. A. and Wanner B. L., Proc. Natl. Acad. Sci. USA, 2000, 97(12): 6640-6645; Zhang Y., et al., Nature Genet., 1998, 20:123-128). Furthermore, for multiple insertions of desired genes in addition to Mu-driven replicative transposition (Akhverdyan V. Z. et al., Appl. Microbiol. Biotechnol., 2011, 91:857-871) and chemically inducible chromosomal evolution based on recA-dependent homologous recombination resulted in an amplification of desired genes (Tyo K. E. J. et al., Nature Biotechnol., 2009, 27:760-765), other methods can be used that utilize different combinations of transposition, site-specific and/or homologous Red/ET-mediated recombinations, and/or P1-mediated generalized transduction (see, for example, Minaeva N. I. et al., BMC Biotechnol., 2008, 8:63; Koma D. et al., Appl. Microbiol. Biotechnol., 2012, 93(2):815-829).

Expression of a gene in a host bacterium can be improved by substituting rare codons (so-called low-usage codons in reference to a host bacterium) for synonymous middle- or high-usage codons, where the codon usage can be defined as the frequency of translation of a codon per unit time in a cell of a host bacterium or an average codon frequency of the sequenced protein-encoding reading frames of a host bacterium (Zhang S. P. et al., Low-usage codons in Escherichia coli, yeast, fruit fly and primates, Gene, 1991, 105(1):61-72). The codon usage per organism can be found in the Codon Usage Database, which is an extended web-version of the CUTG (Codon Usage Tabulated from GenBank, kazusa; Nakamura Y. et al., Codon usage tabulated from the international DNA sequence databases: status for the year 2000, Nucleic Acids Res., 2000, 28(1):292). In Escherichia coli such mutations can include, but are not limited to, the substitution of rare Arg codons AGA, AGG, CGG, CGA for CGT or CGC; rare Ile codon ATA for ATC or ATT; rare Leu codon CTA for CTG, CTC, CTT, TTA or TTG; rare Pro codon CCC for CCG or CCA; rare Ser codon TCG for TCT, TCA, TCC, AGC or AGT; rare Gly codons GGA, GGG for GGT or GGC; and so forth. The substitution of low-usage codons for synonymous high-usage codons can be preferable. The substitution of rare- and/or low-usage codons for synonymous middle- or high-usage codons may be combined with co-expression of the genes which encode tRNAs recognizing rare codons. Codons can be replaced using, for example, the site-specific mutation method for introducing an objective mutation into an objective place of DNA. Examples of the site-specific mutation method include the method utilizing polymerase chain reaction (PCR) (Higuchi R., Using PCR to engineer DNA, 61-70. In: PCR Technology, Erlich H. A. (ed.), Stockton Press, New York (1989); Carter, P., Methods Enzymol., 1987, 154:382-403), and the method utilizing a phage (Kramer W. and Frits H. J., Methods Enzymol., 1987, 154:350-367; Kunkel T. A. et al., Methods Enzymol., 1987, 154:367-382).

When a gene is introduced into a host bacterium, it can be sufficient that the gene is harbored by the modified bacterium so that the gene is expressed in the bacterium. Specifically, it can be sufficient that the gene is introduced so that it is expressed under the control of a promoter sequence (also referred to as a promoter) that functions in the host bacterium. The promoter may be a promoter native to the host bacterium, or a heterogeneous promoter native to the donor organism or even another organism. The promoter may be the native promoter of the gene to be introduced, or a promoter of another gene. As the promoter, for example, a strong promoter as explained herein may also be used.

A terminator sequence (also referred to as a terminator) for termination of gene transcription may be located downstream of the gene. The terminator is not particularly limited so long as it functions in a host bacterium. The terminator may be a terminator native to the host bacterium, or a heterogeneous terminator native to the donor organism or even another organism. The terminator may be the native terminator of the gene to be introduced, or a terminator of another gene.

Furthermore, when two or more of gene copies are introduced, it is sufficient that each gene is harbored by the modified bacterium so that the genes can be expressed in the bacterium. For example, all the genes to be introduced may be present in a single expression vector, or present in the chromosome. Alternatively, the genes may be present in two or more expression vectors, or may be separately present in one or more expression vectors and the chromosome. When the genes are present in different nucleic acid molecules or are present in a sole nucleic acid molecule, the genes may be present in the nucleic acid molecule(s) in such a way that expression of all the genes that are introduced can be attained. Virtually, any way of introducing a gene into a host bacterium can be chosen so long as the expression of the gene can be attained in the bacterium. The phrase "expression can be attained" can refer to when transcription from the DNA can take place such that RNA that complements the DNA as a template can be synthesized. The phrase "expression can be attained" also can refer to when transcription from the DNA can occur such that the RNA that complements the DNA as a template can be synthesized, and translation from the RNA can occur so that a peptide such as, for example, a protein having a desired activity can be produced such that the activity of the protein can be determined.

Vectors, promoters, and terminators native to various microorganisms are disclosed in detail in «Fundamental Microbiology, vol. 8, Genetic Engineering», Kyoritsu Shuppan Co., Ltd (1987), and can be used.

Preferably, a gene is introduced into a host bacterium so that it is expressed under the control of a strong promoter that functions in the bacterium, which promoter is stronger as compared with the native promoter of the gene or a promoter that is native to the host bacterium. Strong promoters providing a high level of gene expression in a bacterium belonging to the family Enterobacteriaceae can be used. Examples of strong promoters that can be used in Enterobacteriaceae bacteria include the lac promoter, the trp promoter, the trc promoter, the tac promoter, and the $P_R$ and the $P_L$ promoters of lambda phage. Furthermore, as the strong promoter, a highly active type of an existing promoter may also be obtained by using various reporter genes. For example, by making the −35 and −10 regions in a promoter region closer to the consensus sequence, the activity of the promoter can be enhanced (WO00/18935). Examples of highly active-type promoter include various tac-like promoters (Katashkina J. I. et al., Russian Federation Patent Application No. 2006134574 A). Methods for evaluating the strength of promoters and examples of strong promoters are described (Goldstein M. A. and Doi R. H., Prokaryotic promoters in biotechnology, *Biotechnol. Annu. Rev.*, 1995, 1:105-128), and so forth.

The transcription efficiency of a gene may be improved further. This can be attained by, for example, introducing a mutation into the promoter region of the gene to obtain a stronger promoter function, thus resulting in the increased transcription level of the gene located downstream of the promoter. Furthermore, it is known that substitution of several nucleotides in the Shine-Dalgarno (SD) sequence, and/or in a spacer region between the SD sequence and the start codon, and/or a sequence immediately upstream and/or downstream from the start codon in the ribosome-binding site considerably affects the translation efficiency of mRNA. For example, a 20-fold range in the expression levels was found, depending on the nature of the three nucleotides preceding the start codon (Gold L. et al., *Annu. Rev. Microbiol.*, 1981, 35:365-403; Hui A. et al., *EMBO J.*, 1984, 3:623-629).

Moreover, the translation efficiency of a gene may be improved further. This can be attained by, for example, replacing the ribosome-binding site (RBS) for the gene on the chromosome with a stronger RBS. The phrase "a stronger RBS" can mean a RBS that provides an improved translation of mRNA as compared with the native, or wild-type RBS of the gene. As an example of a stronger RBS, the RBS of the gene 10 of phage T7 can be used (Olins P. O. et al, *Gene*, 1988, 73:227-235).

As a vector, a vector autonomously replicable in the cell of the host bacterium can be used. The vector is preferably a multi-copy vector, and, preferably, it has a marker gene such as, for example, an antibiotic resistance gene for selection of desired transformants. In addition, the vector may have a promoter and/or a terminator for expressing the introduced gene. The vector may be, for example, a vector derived from a bacterial plasmid, a vector derived from a yeast plasmid, a vector derived from a bacteriophage, cosmid, phagemid, or the like. Examples of vectors suitable for transforming a bacterium belonging to the family Enterobacteriaceae include, but are not limited to, broad-host-range plasmids such as pMW118/119, pBR322, pUC19, and the like. Multiple copies of the gene also can be introduced into the chromosomal DNA of a bacterium by, for example, homologous recombination, Mu-driven integration, or the like. Homologous recombination can be carried out using sequence with multiple copies in the chromosomal DNA. Sequences with multiple copies in the chromosomal DNA include, but are not limited to, repetitive DNA or inverted repeats present at the end of a transposable element. In addition, it is possible to introduce the gene into a transposon and allow it to be transferred to introduce multiple copies of the gene into the chromosomal DNA. By using Mu-driven integration, more than 3 copies of the gene can be introduced into the chromosomal DNA during a single act (Akhverdyan V. Z. et al., *Biotechnol.* (Russian), 2007, 3:3-20).

Introduction of a gene can be confirmed by confirming the presence of the nucleotide sequence of a part of or the entire gene to be introduced. The presence of a nucleotide sequence can be determined by, for example, PCR (Sambrook J., et al.: «Molecular Cloning: A Laboratory Manual», $3^{rd}$ ed., Cold Spring Harbor Laboratory Press, USA (2001)). Introduction of a gene can also be confirmed by confirming the presence of expression of the gene to be introduced. The presence of expression of a gene can be confirmed by confirming the presence of the transcription amount of the gene, or by confirming the presence of the protein encoded by the gene. The presence of the transcription amount of a gene can be confirmed by confirming the presence of mRNA transcribed from the gene. Examples of the method for confirming the presence of mRNA include Northern hybridization, RT-PCR, and so forth (Sambrook J., et al.: «Molecular Cloning: A Laboratory Manual», $3^{rd}$ ed., Cold Spring Harbor Laboratory Press, USA (2001)). The presence of a protein can be determined by, for example, Western blotting using antibodies (Sambrook J., et al.: «Molecular Cloning: A Laboratory Manual», $3^{rd}$ ed., Cold Spring Harbor Laboratory Press, USA (2001)).

The copy number, presence or absence of a gene, can be measured, for example, by restricting the chromosomal DNA followed by Southern blotting using a probe based on the gene sequence, fluorescence in situ hybridization (FISH), and the like. The level of gene expression can be determined by measuring the amount of mRNA transcribed from the gene using various well-known methods, including Northern blotting, quantitative RT-PCR, and the like. The amount of the protein encoded by the gene can be measured by known methods including SDS-PAGE followed by immunoblotting assay (Western blotting analysis), or mass spectrometry analysis of the protein samples, and the like.

Methods for manipulation with recombinant molecules of DNA and molecular cloning such as preparation of plasmid DNA, digestion, ligation and transformation of DNA, selection of an oligonucleotide as a primer, incorporation of mutations, and the like may be ordinary methods well-known to the persons of ordinary skill in the art. These methods are described in, for example, Sambrook J., Fritsch E. F. and Maniatis T., "Molecular Cloning: A Laboratory Manual", $2^{nd}$ ed., Cold Spring Harbor Laboratory Press (1989) or Green M. R. and Sambrook J. R., "Molecular Cloning: A Laboratory Manual", $4^{th}$ ed., Cold Spring Harbor Laboratory Press (2012); Bernard R. Glick, Jack J. Pasternak and Cheryl L. Patten, "Molecular Biotechnology: principles and applications of recombinant DNA", $4^{th}$ ed., Washington, DC, ASM Press (2009).

The bacterium that can be used in the method as described herein also can be modified to attenuate expression of, at least, one gene that encodes a phosphatase (EC 3.1.3), examples of which are listed, for example, in the UniProtKB Database (enzyme.expasy.org). According to the method, the bacterium can be modified to attenuate expression of one or more of an aphA gene, a cysQ gene, and a cpdB gene. In one example, the bacterium can be modified to attenuate expression of an aphA gene. The bacterium having the aphA gene, the expression of which is attenuated, can be modified further to attenuate expression of a cysQ gene or/and a cpdB gene. In another example, the bacterium can be modified to attenuate expression of a cysQ gene. The bacterium having the cysQ gene, the expression of which is attenuated, can be modified further to attenuate expression of an aphA gene or/and a cpdB gene.

The explanations given below to the attenuation of expression of an aphA gene can also be similarly applied to any gene having the attenuated expression in the bacterium that can be used in the method as described herein. Examples of such genes include, but are not limited to, the cysQ and cpdB genes.

The phrase "a bacterium has been modified to attenuate expression of an aphA gene" can mean that the bacterium has been modified in such a way that in the modified bacterium expression of the aphA gene is attenuated. As an example, the expression of the aphA gene can be attenuated due to inactivation of the aphA gene.

The phrase "an aphA gene is inactivated" can mean that the modified gene encodes a completely inactive or non-functional protein AphA as compared with the bacterium that harbors a wild-type or non-modified aphA gene. It is also acceptable that the modified DNA region is unable to naturally express the aphA gene due to deletion of a part of the gene or deletion of the entire gene, replacement of one base or more in the nucleotide sequence of the gene to cause an amino acid substitution in the protein encoded by the gene (missense mutation), introduction of a stop codon (nonsense mutation), deletion of one or two bases to cause a reading frame shift of the gene, insertion of a drug-resistance gene and/or transcription termination signal, or modification of an adjacent region of the gene, including sequences controlling gene expression such as promoter(s), enhancer(s), attenuator(s), ribosome-binding site(s), etc. Inactivation of the gene can also be performed by, for example, conventional methods such as a mutagenesis treatment using UV irradiation or nitrosoguanidine (N-methyl-N'-nitro-N-nitrosoguanidine), site-directed mutagenesis, gene disruption using homologous recombination, and/or insertion-deletion mutagenesis (Yu D. et al., *Proc. Natl. Acad. Sci. USA*, 2000, 97(11):5978-5983; Datsenko K. A. and Wanner B. L., *Proc. Natl. Acad. Sci. USA*, 2000, 97(12):6640-6645; Zhang Y. et al., *Nature Genet.*, 1998, 20:123-128) based on "Red/ET-driven integration" or "λRed/ET-mediated integration".

The phrase "expression of an aphA gene is attenuated" can mean that the modified bacterium contains a region operably linked to the gene, including sequences controlling gene expression such as promoters, enhancers, attenuators and transcription termination signals, ribosome-binding sites, and other expression control elements, which is modified resulting in the decrease of the expression level of the aphA gene; and other examples (see, for example, WO95/34672; Carrier T. A. and Keasling J. D., *Biotechnol. Prog.*, 1999, 15:58-64). The phrase "operably linked" with reference to a gene can mean that the regulatory region(s) is/are linked to the nucleotide sequence of a nucleic acid molecule or a gene in such a manner so that the expression (for example, enhanced, increased, constitutive, basal, antiterminated, attenuated, deregulated, decreased, or repressed expression) of the nucleotide sequence can take place, specifically, the expression of a gene product encoded by the nucleotide sequence.

The phrase "expression of an aphA gene is attenuated" also can mean that the amount of an expression product of the aphA gene, such as the amount of mRNA of the gene or the amount of the AphA protein encoded by the gene, in the modified bacterium, in which expression of the aphA gene is attenuated, is reduced, for example, to 50% or less, 20% or less, 10% or less, 5% or less, or even 0% of that amount in the non-modified bacterium.

The phrase "a bacterium has been modified to attenuate expression of an aphA gene" also can mean that the bacterium has been modified in such a way that in the modified bacterium the total enzymatic activity of the corresponding gene protein product such as the AphA protein is decreased as compared with that activity in the non-modified bacterium. The bacterium can be modified so that the activity of the AphA protein per cell is decreased, for example, to 50% or less, 20% or less, 10% or less, 5% or less, or even 0% of that activity in the non-modified bacterium.

Examples of a non-modified bacterium serving as a reference for the above comparisons can include wild-type strains of a bacterium belonging to the genus *Escherichia* such as the *E. coli* strain K-12 substr. MG1655 (ATCC 47076), *E. coli* W3110 strain (ATCC 27325), or a bacterium belonging to the genus *Pantoea* such as the *P. ananatis* AJ13355 strain (FERM BP-6614), and so forth.

Expression of an aphA gene can be attenuated by replacing an expression control sequence of the gene, such as a promoter in the chromosomal DNA, with a weaker one. For example, it is possible to introduce one or more nucleotide substitutions in a promoter region of the gene and thereby modify the promoter to be weakened as disclosed in WO0018935 A1. Furthermore, it is known that substitution of several nucleotides in the Shine-Dalgarno (SD) sequence, and/or in a spacer region between the SD sequence and the start codon, and/or a sequence immediately upstream and/or downstream from the start codon in the ribosome-binding site considerably affects the translation efficiency of mRNA. This modification of the RBS may be combined with decreasing transcription of the aphA gene.

Expression of an aphA gene can also be attenuated by inserting a transposon or an insertion sequence (IS) into the encoding region of the gene (U.S. Pat. No. 5,175,107) or in the region controlling gene expression, or by conventional methods such as mutagenesis with ultraviolet (UV) irradiation or nitrosoguanidine (N-methyl-N'-nitro-N-nitrosoguanidine, NTG). Furthermore, the incorporation of a site-specific mutation can be conducted by known chromosomal editing methods based, for example, on λRed/ET-mediated recombination (Datsenko K. A. and Wanner B. L., *Proc. Natl. Acad. Sci. USA*, 2000, 97(12):6640-6645).

The aphA gene (synonyms: ECK4047, hobH, JW4015, napA, yjbP) of *E. coli* encodes class B acid phosphatase, AphA (EC 3.1.3.2; NCBI, GenBank, accession No. NC_000913.3, nucleotide positions: 4269414 to 4270127, Gene ID: 948562), and is located between the yjbS gene in the opposite strand and the yjbQ gene in the same strand of the chromosome of *E. coli* strain K-12. The nucleotide sequence of the aphA gene (SEQ ID NO: 1) and the amino acid sequence of the AphA protein (SEQ ID NO: 2) encoded by the aphA gene native to *E. coli* strain K-12 substr. MG1655 are known. Moreover, the amino acid homologues of AphA native to other bacterial species belonging to the family Enterobacteriaceae are known also, such as, for example, the homologues native to the species *Shigella flexneri* (identity with the AphA native to *E. coli* strain K-12 substr. MG1655 (SEQ ID NO: 2): 100%), *Shigella sonnei* (identity: 99%), *Citrobacter freundii* (identity: 91%), *Salmonella enterica* (identity: 89%), *Kluyvera cryocrescens* and *Enterobacter cloacae* (identity: 84%), *Klebsiella michiganensis* and *Raoultella planticola* (identity: 83%), *Pantoea* sp. 1.19 (identity: 75%), and so forth (see, for example, the NCBI database, National Center for Biotechnology Information, ncbi.nlm.nih.gov/protein). Therefore, the AphA protein native to *E. coli* strain K-12 substr. MG1655 and the aphA gene encoding it can also have, respectively, proteins and genes that are homologues of the protein having the amino acid sequence shown in SEQ ID NO: 2 and the nucleotide sequence shown in SEQ ID NO: 1.

The cysQ gene (synonyms: amt, amtA, ECK4210, JW4172) of *E. coli* encodes 3'(2'),5'-bisphosphate nucleotidase, CysQ (EC 3.1.3.7; NCBI, GenBank, accession No. NC_000913.3, nucleotide positions: 4436755 to 4437495, Gene ID: 948728), and it is located between the cpdB gene in the opposite strain and the ytfI gene in the same strand of the chromosome of *E. coli* strain K-12. The nucleotide sequence of the cysQ gene (SEQ ID NO: 3) and the amino acid sequence of the CysQ protein (SEQ ID NO: 4) encoded by the cysQ gene native to *E. coli* strain K-12 substr. MG1655 are known. Moreover, the amino acid homologues of CysQ native to other bacterial species belonging to the family Enterobacteriaceae are known also, such as, for example, the homologues native to the species *Shigella sonnei* (identity with the CysQ native to *E. coli* strain K-12 substr. MG1655 (SEQ ID NO: 4): 99%), *Citrobacter amalonaticus* (identity: 91%), *Enterobacter cloacae* (identity: 90%), *Salmonella enterica* and *Klebsiella oxytoca* (identity: 88%), *Pluralibacter gergoviae* (identity: 87%), *Pantoea ananatis* (identity: 81%), and so forth (see, for example, the NCBI database). Therefore, the CysQ protein native to *E. coli* strain K-12 substr. MG1655 and the cysQ gene encoding it can also have, respectively, proteins and genes that are homologues of the protein having the amino acid sequence shown in SEQ ID NO: 4 and the nucleotide sequence shown in SEQ ID NO: 3.

The cpdB gene (synonyms: ECK4209; JW4171) of *E. coli* encodes 2',3'-cyclic-nucleotide 2'-phosphodiesterase/3'-nucleotidase, CpdB (EC 3.1.4.16, 3.1.3.6; NCBI, GenBank, accession No. NC_000913.3, nucleotide positions: 4434622 to 4436565, complement), Gene ID: 948729), and it is located between the cysQ gene and the ytfH gene in the opposite strain of the chromosome of *E. coli* strain K-12. The nucleotide sequence of the cpdB gene (SEQ ID NO: 5) and the amino acid sequence of the CpdB protein (SEQ ID NO: 6) encoded by the cpdB gene native to *E. coli* strain K-12 substr. MG1655 are known. Moreover, the amino acid homologues of CpdB native to other bacterial species belonging to the family Enterobacteriaceae are known also, such as, for example, the homologues native to the species *Shigella sonnei* and *Shigella flexneri* (identity with the CpdB native to *E. coli* strain K-12 substr. MG1655 (SEQ ID NO: 6): 99%), *Citrobacter freundii* and *Salmonella enterica* (identity: 91%), *Kluyvera ascorbata* (identity: 89%), *Enterobacter cloacae* (identity: 88%), *Klebsiella pneumonia* (identity: 87%), *Pantoea ananatis* (identity: 75%), and so forth (see, for example, the NCBI database). Therefore, the CpdB protein native to *E. coli* strain K-12 substr. MG1655 and the cpdB gene encoding it can also have, respectively, proteins and genes that are homologues of the protein having the amino acid sequence shown in SEQ ID NO: 6 and the nucleotide sequence shown in SEQ ID NO: 5.

The explanations given below to the variants of the aphA gene native to an *E. coli* strain K-12 substr. MG1655 and encoding the AphA protein can also be similarly applied to any gene and protein encoded by that gene, including genes and proteins that are native to other bacterial species belonging to the family Enterobacteriaceae, that can be used in the method as described herein.

There may be differences in DNA sequences between the bacterial families, genera, species or strains. Therefore, an aphA gene is not limited to the gene shown in SEQ ID NO: 1, but may include genes which are variant nucleotide sequences of or homologous to SEQ ID NO: 1 and encode variants of the AphA protein.

The phrase "a variant protein" can mean a protein which has one or more mutations in the sequence as compared with the amino acid sequence shown in SEQ ID NO: 2, whether they are substitutions, deletions, insertions, and/or additions of one or several amino acid residues, but still maintains activity or function of the protein, or the three-dimensional structure of the variant protein is not significantly changed relative to the non-modified protein such as, for example, the wild-type protein AphA having the amino acid sequence shown in SEQ ID NO: 2. The number of changes in a variant protein depends on the position of amino acid residue(s) in the three-dimensional structure of the protein or the type of amino acid residue(s). It can be, but is not strictly limited to, 1 to 50, in another example 1 to 40, in another example 1 to 30, in another example 1 to 20, in another example 1 to 15, in another example 1 to 10, and in another example 1 to 5, in SEQ ID NO: 2. This is possible because amino acids can have high homology to one another so that the activity or function of the protein is not affected by such a change, or the three-dimensional structure of the protein is not significantly changed relative to the non-modified protein such as, for example, the wild-type protein. Therefore, the variant proteins encoded by variant nucleotide sequences of the aphA gene may have a homology, defined as the parameter "identity" when using the computer program blastp, of not less than 60%, not less than 70%, not less than 75%, not less than 80%, not less than 85%, not less than 90%, not less than 95%, not less than 96%, not less than 97%, not less than 98%, or not less than 99% with respect to the entire amino acid sequence shown in SEQ ID NO: 2 as long as the activity or function of the protein is maintained, or the three-dimensional structure of the variant protein is not significantly changed relative to the non-modified protein such as, for example, the wild-type protein AphA having the amino acid sequence shown in SEQ ID NO: 2.

In this specification, "homology" may mean "identity", that is the identity of amino acid residues or nucleotides. The sequence identity between two sequences is calculated as the ratio of residues matching in the two sequences when aligning the two sequences so as to achieve a maximum alignment with each other.

The exemplary substitution, deletion, insertion, and/or addition of one or several amino acid residues can be a conservative mutation(s). The representative conservative mutation can be a conservative substitution. The conservative substitution can be, but is not limited to, a substitution, wherein substitution takes place mutually among Phe, Trp and Tyr, if the substitution site is an aromatic amino acid; among Ala, Leu, Ile and Val, if the substitution site is a hydrophobic amino acid; between Glu, Asp, Gln, Asn, Ser, His and Thr, if the substitution site is a hydrophilic amino acid; between Gln and Asn, if the substitution site is a polar amino acid; among Lys, Arg and His, if the substitution site is a basic amino acid; between Asp and Glu, if the substitution site is an acidic amino acid; and between Ser and Thr, if the substitution site is an amino acid having hydroxyl group. Examples of conservative substitutions include substitution of Ser or Thr for Ala, substitution of Gln, His or Lys for Arg, substitution of Glu, Gln, Lys, His or Asp for Asn, substitution Asn, Glu or Gln for Asp, substitution of Ser or Ala for Cys, substitution Asn, Glu, Lys, His, Asp or Arg for Gln, substitution Asn, Gln, Lys or Asp for Glu, substitution of Pro for Gly, substitution Asn, Lys, Gln, Arg or Tyr for His, substitution of Leu, Met, Val or Phe for Ile, substitution of Ile, Met, Val or Phe for Leu, substitution Asn, Glu, Gln, His or Arg for Lys, substitution of Ile, Leu, Val or Phe for Met, substitution of Trp, Tyr, Met, Ile or Leu for Phe, substitution of Thr or Ala for Ser, substitution of Ser or Ala for Thr, substitution of Phe or Tyr for Trp, substitution of His, Phe or Trp for Tyr, and substitution of Met, Ile or Leu for Val.

The exemplary substitution, deletion, insertion, and/or addition of one or several amino acid residues also can be a non-conservative mutation(s) provided that the mutation(s) is/are compensated by one or more secondary mutation(s) in the different position(s) of amino acids sequence so that the activity or function of the protein is maintained, or the three-dimensional structure of the variant protein is not significantly changed relative to the non-modified protein such as, for example, the wild-type protein.

The calculation of a percent identity of a polypeptide can be carried out using the algorithm blastp. More specifically, the calculation of a percent identity of a polypeptide can be carried out using the algorithm blastp in the default settings of Scoring Parameters (Matrix: BLOSUM62; Gap Costs: Existence=11 Extension=1; Compositional Adjustments: Conditional compositional score matrix adjustment) provided by National Center for Biotechnology Information (NCBI). The calculation of a percent identity of a polynucleotide can be carried out using the algorithm blastn. More specifically, the calculation of a percent identity of a polynucleotide can be carried out using the algorithm blastn in the default settings of Scoring Parameters (Match/Mismatch Scores=1, −2; Gap Costs=Linear) provided by NCBI.

An aphA gene encoding an AphA protein can be a variant nucleotide sequence. The phrase "a variant nucleotide sequence" can mean the nucleotide sequence which encodes a variant protein using any synonymous amino acid codons according to the standard genetic code table (see, for example, Lewin B., "Genes VIII", 2004, Pearson Education, Inc., Upper Saddle River, NJ 07458). Therefore, an aphA gene encoding an AphA protein can be a variant nucleotide sequence due to the degeneracy of the genetic code.

The phrase "a variant nucleotide sequence" also can mean, but is not limited to, a nucleotide sequence that is able to hybridize under stringent conditions with the nucleotide sequence complementary to the sequence shown in SEQ ID NO: 1 or a probe that can be prepared from the nucleotide sequence that encodes a protein having the amino acid sequence shown in SEQ ID NO: 2. Stringent conditions can include those conditions under which a specific hybrid, for example, a hybrid having homology, defined as the parameter "identity" when using the computer program blastn, of not less than 60%, not less than 70%, not less than 75%, not less than 80%, not less than 85%, not less than 90%, not less than 95%, not less than 96%, not less than 97%, not less than 98%, or not less than 99% is formed, and a non-specific hybrid, for example, a hybrid having homology lower than the above is not formed. For example, stringent conditions can be exemplified by washing one time or more, or in another example, two or three times, at a salt concentration of 1×SSC (standard sodium citrate or standard sodium chloride), 0.1% SDS (sodium dodecyl sulfate) at 60° C., 0.1×SSC, 0.1% SDS at 60° C., or 0.1×SSC, 0.1% SDS at 65° C. Duration of washing can depend on the type of membrane used for the blotting and, as a rule, should be what is recommended by the manufacturer. For example, the recommended duration of washing for the Amersham Hybond™-N+ positively charged nylon membrane (GE Healthcare) under stringent conditions is 15 minutes. The washing step can be performed 2 to 3 times. As the probe, a part of the sequence complementary to the sequence shown in SEQ ID NO: 1 may also be used. Such a probe can be produced by PCR (polymerase chain reaction; refer to White T. J. et al., The polymerase chain reaction, *Trends Genet.*, 1989, 5:185-189) using oligonucleotides as primers prepared on the basis of the sequence shown in SEQ ID NO: 1 and a DNA fragment containing the nucleotide sequence as a template. The length of the probe is recommended to be >50 bp; it can be suitably selected depending on the hybridization conditions and is usually 100 bp to 1 kbp. For example, when a DNA fragment having a length of about 300 bp is used as the probe, the washing conditions after the hybridization can be, for example, 2×SSC, 0.1% SDS at 50° C., 60° C., or 65° C.

As the aphA gene native to the species *E. coli* and encoding the AphA protein has already been elucidated (see above), the genes native to other bacterial species of the family Enterobacteriaceae and encoding the AphA protein, and the variant nucleotide sequences of the aphA gene encoding variant proteins of the AphA protein can be obtained by PCR utilizing a bacterium of the family Enterobacteriaceae and oligonucleotide primers prepared based on the nucleotide sequence of an aphA gene native to the bacterium; or the site-directed mutagenesis method by treating a DNA containing the wild-type aphA gene, in vitro, for example, with hydroxylamine, or a method for treating a microorganism, for example, a bacterium belonging to the family Enterobacteriaceae harboring the wild-type aphA gene with ultraviolet (UV) irradiation or a mutating agent such as N-methyl-N'-nitro-N-nitrosoguanidine (NTG) and nitrous acid usually used for the such treatment; or chemically synthesized as full-length gene structure.

The phrase "wild-type", which can be equivalent to the phrases "native" and "natural" as used herein with reference to a gene (for example, "a wild-type gene") and a protein (for example, "a wild-type protein") can mean, respectively, a native gene and a native protein that exist, and/or is expressed naturally in, and/or produced by a wild-type bacterium, for example, a wild-type strain of a bacterium belonging to the family Enterobacteriaceae such as, for example, the *E. coli* MG1655 strain (ATCC 47076), the *E. coli* W3110 strain (ATCC 27325), the *P. ananatis* AJ13355 strain (FERM BP-6614), and so forth. As a protein is encoded by a gene, "a wild-type protein" can be encoded by "a wild-type gene" natively or naturally occurring in the genome of a wild-type bacterium.

The bacterium that can be used in the method as described herein can be obtained by introduction of the aforementioned DNAs encoding proteins having the desired activities into the bacterium that already had been modified to attenuate expression of one or more aforementioned DNAs encoding phosphatases. Alternatively, the bacterium can be obtained by attenuating expression of one or more aforementioned DNAs encoding phosphatases in the bacterium that already had been modified to produce proteins having the desired activities.

The bacterium can have, in addition to the properties already mentioned, other specific properties such as various nutrient requirements, drug resistance, drug sensitivity, and drug dependence, without departing from the scope of the present invention.

A method for enzymatic sulfurylation of a substrate as described herein includes the steps of reacting the substrate with PAPS in a medium containing a bacterium belonging to the family Enterobacteriaceae to produce a sulfated derivative of the substrate (can also be referred to as a target compound) and collecting the sulfated derivative from the medium. The method may include, optionally, the step of purifying the sulfated derivative from the medium so that the target compound can be obtained at the desired grade of purity, and/or other required steps.

The step of reacting a substrate using the method as described herein can be performed under conditions suitable for the functioning of a protein having the desired activity so that a sulfated derivative of the substrate, or a target compound can be produced. The medium that can be used in the method can be any medium so long as a substrate can be sulfurylated in the medium to produce a sulfated derivative thereof using the method. The medium can contain the components that are required for the sulfurylation of the substrate using the method as described herein, and these include, at least, a solvent, a bacterium belonging to the family Enterobacteriaceae, PAPS, and a substrate. In addition to these components, the medium can contain one or more other ingredients such as, for examples, organic and/or inorganic salt(s), acidic or alkaline substance(s), surfactant(s), p-nitrophenyl sulfate (pNPS), proteins, including enzymes, and so forth. With reference to the solvent, a water-based medium can be used, in which, at least, a protein having sulfotransferase activity can function so that activity of the protein can be determined. For example, a culture medium, in which the bacterium that can be used in the method has been cultivated, may be used for the enzymatic sulfurylation of a substrate, provided that the culture medium is supplemented with components that are required for the sulfurylation of the substrate. Moreover, the composition of the medium can be chosen appropriately so that other protein(s), for example, a protein having heparosan-N-sulfate-glucouronate 5-epimerase activity and/or a protein having 3'-phosphoadenosine-5'-phosphosulfate-sulfotransferase activity, and so forth, also can function.

As the bacterium that can be used in the method as described herein has been modified to produce, at least, a protein having sulfotransferase activity, and it may be modified further to produce a protein having heparosan-N-sulfate-glucouronate 5-epimerase activity or/and a protein having 3'-phosphoadenosine-5'-phosphosulfate-sulfotransferase activity, the proteins having the above activities can be used without isolation and/or purification from the bacterial cells and/or culture medium in which the bacterium was cultured. That is, a culture medium containing the bacterium that has been modified as described herein can be used so long as the activity of a protein having the desired activity can be determined in the medium or a sulfated derivative of the substrate can be produced using the method. A culture medium that can be used can contain disrupted cells of the bacterium (so-called crude cell lysate) so that a protein having the desired activity can be used more effectively. Methods of cells disruption are well-known in the art, and these include, for example, mechanical disruption, liquid homogenization (including the French press), high frequency sound waves (so-called ultrasonic lysis), freeze-thaw cycles, manual grinding, and so forth.

The conditions for enzymatic sulfurylation of a substrate using the method as described herein can be appropriately chosen and adjusted by referring to the properties of proteins that can be used in the method, which properties are well-known to the persons skilled in the art and can be found in, for example, The Comprehensive Enzyme Information System (Brenda, brenda-enzymes.org) and the UniProtKB Database (enzyme.expasy.org). For example, when a protein native to a mammalian species is used, the sulfurylation can be performed for from 24 to 72 hours at the temperature from 25 to 35° C., and the pH can be maintained at from 6.5 to 7.5.

A bacterium belonging to the family Enterobacteriaceae that can be used in the method as described herein can be cultivated under the conditions suitable for cultivating a bacterium chosen for the use in the method. For example, when a bacterium belonging to the genus *Escherichia* is cultivated, the cultivation can be performed under aerobic conditions for from 16 to 72 hours, for from 16 to 24 hours or for from 32 to 48 hours, the culture temperature during cultivation can be controlled within from 30 to 45° C. or within from 30 to 37° C., and the pH can be adjusted between 5 and 8 or between 6 and 7.5. The pH can be adjusted using an inorganic or organic acidic or alkaline substance such as urea, calcium carbonate or ammonia gas.

The culture medium can be either a synthetic or natural medium such as a typical A medium that contains a carbon source, a nitrogen source, a sulfur source, a phosphorus source, inorganic ions, and other organic and inorganic components as required. As the carbon source, saccharides such as glucose, sucrose, lactose, galactose, fructose, arabinose, maltose, xylose, trehalose, ribose, and hydrolyzates of starches; alcohols such as ethanol, glycerol, mannitol, and sorbitol; organic acids such as gluconic acid, fumaric acid, citric acid, malic acid, and succinic acid; fatty acids, and the like can be used. As the nitrogen source, inorganic ammonium salts such as ammonium sulfate, ammonium chloride, and ammonium phosphate; organic nitrogen such as that of soy bean hydrolysate; ammonia gas; aqueous ammonia; and the like can be used. Furthermore, peptone, yeast extract, meat extract, malt extract, corn steep liquor, and so forth can also be utilized. The medium may contain one or more types of these nitrogen sources. The sulfur source can include ammonium sulfate, magnesium sulfate, ferrous sulfate, manganese sulfate, and the like. The medium can contain a phosphorus source in addition to sulfur A the carbon source, the nitrogen source and the sulfur source. As the phosphorus source, potassium dihydrogen phosphate, dipotassium hydrogen phosphate, phosphate polymers such as pyrophosphoric acid and so forth can be utilized. Vitamins such as vitamin B1, vitamin B2, vitamin B6, nicotinic acid, nicotinamide, vitamin B12, required substances, for example, organic nutrients such as nucleic acids such as adenine and RNA, amino acids, peptone, casamino acid, yeast extract, and the like may be present in appropriate, even if trace, amounts. Other than these, small amounts of calcium phosphate, iron ions, manganese ions, and so forth may be added, if necessary.

A sulfated derivative of the substrate can be produced in a free form or as a salt thereof, or as a mixture of these. For example, sodium, potassium, ammonium, calcium, and the like salts of the target compound can be produced by the method. This is possible, because sulfo group ($-SO_3H$) can react under the sulfurylation conditions with a neutralizing agent such as, for example, an alkaline substance in a typical acid-base neutralization reaction to form a salt that is the chemical feature of sulfo group-containing molecules which is apparent to the person of ordinary skill in the art.

After the step of reacting the substrate, a sulfated derivative of the substrate can be collected from the medium using conventional techniques such as, for example, concentration, precipitation, crystallization, ion-exchange chromatography, medium or high pressure liquid chromatography, or a combination of these, which are well-known to the persons of ordinary skill in the art. Furthermore, the sulfated derivative collected from the medium can be purified so that the target compound can be obtained at the desired grade of purity such as, for example, of not less than 30%, not less than 40%, not less than 50%, not less than 60%, not less than 70%, not less than 80%, not less than 90%, not less than 95%, not less than 96%, not less than 97%, not less than 98%, not less than 99%, or not less than 99.9%. The purity may be expressed, for example, in terms of weight-by-weight (w/w), and the like.

For example, when heparin is obtained as a target compound using the method for enzymatic sulfurylation as described herein, the heparin can be collected from the medium using, for example, the procedure which is described in van der Meer J. Y. et al., 2017, and in the references cited therein. In particular, firstly, the heparin may be precipitated from the medium using a quaternary ammonium salt such as, for example, Hyamine® 1622. Then, the precipitated Hyamine®-heparin complex can be extracted using concentrated NaCl solution to obtain heparin sodium salt. The heparin sodium salt then can be subjected to anion-exchange chromatography under the control of temperature, pH and salt concentration to recover heparin fractioned according to charge and the specific activity. At this stage, heparin at sufficient grade of purity can be obtained usually. The heparin can be obtained, for example, as a low molecular weight heparin (abbreviated as "LMWH"). Low molecular weight heparin can mean, for example, a fraction of a molecular weight of 1000 to 10000 Da (average molecular weight, 4000 to 6000 Da). LMWH has an advantage that it shows less adverse reaction of hemorrhage as compared with a non-fractionated heparin.

Optionally, the heparin can be purified further by applying the precipitation using organic solvents such as, for example, methanol, ethanol, propanol or acetone, and the bleaching using, for example, potassium permanganate ($KMnO_4$), hydrogen peroxide ($H_2O_2$), peracetic acid ($CH_3CO_3H$), sodium hypochlorite (NaClO) or ozone ($O_3$). The heparin can be purified finally by the precipitation from high percentage methanol or ethanol. If required, the precipitated heparin can be dried under vacuum at the temperature from 40 to 75° C.

It is also acceptable that when heparin is obtained as a target compound using the method for enzymatic sulfurylation as described herein, the heparin may also be subjected to a depolymerization step. The depolymerization can be performed, for example, by using nitrous acid or by the photolysis method, or enzymatically by applying heparinase I, II or III, or a combination of them. Degree of the depolymerization is not particularly limited. The depolymerization may be performed so that heparin having a molecular weight of, for example, 1000 to 35000 Da is obtained.

EXAMPLES

The present invention will be more specifically explained with reference to the following non-limiting examples.

Example 1. Studying of Stability of PAP and PAPS in Cell Lysate of E. coli Strain Origami® 2 (ΔptrA ΔhslU) Having Deleted Phosphatase-Encoding Genes 1.1. The E. coli K-12 strain Origami® 2 (ΔptrA ΔhslU).

The stability of PAP and PAPS was studied in crude cell lysate of E. coli K-12 strain Origami® 2 (ΔptrA ΔhslU), which has been modified further to delete one or more phosphatase-encoding genes selected from aphA, cysQ and cpdB genes. It is known that enzymatic activity of proteins that are synthesized in or produced by a cell can be affected by the proper formation of protein disulfide bonds (see, for example, Ke N. and Berkmen M., Production of disulfide-bonded proteins in Escherichia coli, Curr. Protoc. Mol. Biol., 2014, 108:16.1B.1-21). Therefore, an E. coli K-12 strain Origami® 2 (Merck, cat. No. 71344-3) having the genotype Δ(ara-leu)7697 ΔlacX74 ΔphoA PvuII phoR araD139 ahpC galE galK rpsL F'[lac⁺lacI$^q$ pro] gor522:Tn10 trxB (Str$^R$, Tet$^R$) was chosen for the production of a sulfoptransferase and heparosan-N-sulfate-glucouronate 5-epimerase. The strain has mutations in genes encoding thioredoxin reductase (trxB) and glutathione reductase (gor), which enhance considerably formation of disulfide bonds in E. coli cytoplasm.

It is known also that sulfoptransferase and heparosan-N-sulfate-glucouronate 5-epimerase can be produced effectively in E. coli bacteria as maltose binding protein (MBP)-tagged proteins (see, for example, Bethea H. N. et al., Redirecting the substrate specificity of heparan sulfate 2-O-sulfotransferase by structurally guided mutagenesis, Proc. Natl. Acad. Sci. USA, 2008, 105(48):18724-18729; Li K. et al., Using engineered 2-O-sulfotransferase to determine the activity of heparan sulfate C5-epimerase and its mutants, J. Biol. Chem., 2010, 285(15):11106-11113). However, it may be desirable to improve further the effectiveness of the production of target proteins in crude cell lysates. This can be attained by, for example, decreasing the proteolytic degradation of MBP-tagged proteins. In particular, one or more protease-encoding genes can be deleted in the bacterium expressing the proteins. We found that stability of MBP-tagged proteins in crude lysates of E. coli cells can be significantly improved by deleting the ptrA and hslU genes encoding periplasmic protease III and ATPase component of the Hs1VU protease, respectively.

Thus, the E. coli K-12 strain Origami® 2 (ΔptrA ΔhslU) was chosen as an optimal host strain for production of the MBP-tagged proteins and studying of stability of PAP and PAPS in crude cell lysates.

1.2. Construction of E. coli Δ2-5-Strains

The ptrA, hslU, cysQ, cpdB, and aphA genes were deleted one by one in the chromosome of E. coli K-12 strain Origami® 2. The in-frame gene deletion method (also known as Dual-In/Out method) was used (Minaeva N. I. et al., BMC Biotechnol., 2008, 8:63). The constructed Δ2-5-strains are described in Table 1.

1.3. Preparation of Crude Cell Lysates

The Δ2-5-strains were each grown in 10 mL of LB-medium (Sambrook, J. and Russell, D. W. "Molecular Cloning: A Laboratory Manual", 3rd ed., Cold Spring Harbor Laboratory Press (2001)) at 37° C. overnight (for about 16 hours) in 50-mL test tubes. Then, cells were harvested by centrifugation (5000 rpm), re-suspended in 0.3 mL of buffer A (100 mM Tris-HCl, pH 7.5; 10% (v/v) glycerol), and disrupted by sonication. Fractions of insoluble cell components were precipitated by centrifugation (13000 rpm). Soluble fractions of crude cell lysates (so-called supernatants) were transferred into new vials and used for studying the stability of PAP and PAPS in a PAP(S)-stability assay.

1.4. PAP(S)-Stability Assay

Each reaction mixture (100 μL) contained: 50 mM MES (2-(N-morpholino) ethanesulfonic acid), pH 7.0; 1 mM $MgCl_2$; Triton x 100, 1% (v/v); and 0.4 mg/mL of PAP or PAPS. A soluble fraction of a crude cell lysate (Example 1.3) was added up to the final protein concentration of 2.5 mg/mL in reaction mixture. As a control, water was used instead of the lysate. Each reaction mixture was incubated at 30° C. for the time-period indicated in the Tables 2 and 3, and then analyzed using HPLC method. Conditions of the HPLC analysis were as follows:
Equipment: Alliance Waters,
Column: TSK GEL DEAE-5PW 2×75 mm, 10 m,
Detection: UV-detector (dual absorbance detector), detection at 235 nm for NS and NS2S, detection at 254 nm for PAP and PAPS, wherein NS means α-ΔUA-[1→4]-GlcNS and NS2S means α-ΔUA-2S-[1→4]-GlcNS, wherein ΔUA means 4-deoxy-L-threo-hex-4-enopyranosyluronic acid and GlcNS means N-sulfo-D-glucosamine,
Elution gradient: 0 min-0% B, 15 min-5% B, 20 min-30% B, 30 min-100% B, for 30 min-to 0% B, wherein the elution buffer A is 2.56 mM $NaH_2PO_4$ (pH 3.0, adjusted with $H_3PO_4$), 5% acetonitrile; and the elution buffer B is 2.56 mM $NaH_2PO_4$ (pH 3.0, adjusted with $H_3PO_4$), 0.5 M $LiCl_2$,
Temperature: 40° C.,
Elution rate: 0.2 mL/min,
Injection volume: 10 μL,
Injection time: 50 min,
Pressure: 140-160 psi,
Calibration samples: 1-200 mg/L,
Detection limit: 0.005 mg/L.
Elution time: PAP (19.42 min), NS (21.94 min), PAPS (26.02 min), NS2S (28.91 min).

The results of the PAP(S)-stability assay are shown in Tables 2 and 3. As one can see from the Table 2, PAP is notably unstable in a crude cell lysate of the Δ2-strain, it was degraded completely within 22 hours. Deletion of cysQ gene in Δ2-strain to obtain the Δ3-strain resulted in improvement of PAP stability; however, the entire PAP was degraded within 22 hours. Deletion of cpdB gene in Δ3-strain to obtain the Δ4-strain resulted in considerable improvement of PAP stability; about 25% of the PAP was maintained in the reaction mixture after 22 hours of incubation. Deletion of aphA gene in Δ4-strain to obtain the Δ5-strain resulted in two-times greater improvement of PAP stability; about 50% of the PAP was maintained in the reaction mixture after 22 hours of incubation. Thus, stability of PAP can be improved by the deletion of one or more genes encoding AphA, CysQ, and CpdB.

As one can see from the Table 3, PAPS is notably unstable in a crude cell lysate of the Δ2-strain; it was degraded completely within 22 hours. Deletion of cysQ gene in Δ2-strain to obtain the Δ3-strain resulted in ten-times greater improvement of PAPS stability within 22 hours. Deletion of cpdB gene in Δ3-strain to obtain the Δ4-strain did not result in improvement of PAPS stability. Deletion of aphA gene in Δ4-strain to obtain the Δ5-strain resulted in two-times greater improvement of PAPS stability. Thus, stability of PAPS can be improved by the deletion of one or two genes encoding AphA and CysQ.

Example 2. Enzymatic Sulfurylation of Low Molecular Weight Heparosan N-Sulfate Using PAPS as a Donor of Sulfo Group The enzymatic sulfurylation of low molecular weight heparosan N-sulfate (abbreviated as "LMWHS") was performed using PAPS as a donor of sulfo group and crude cell lysates of Δ2-5-strains that can produce heparosan sulfate 2-O-sulfotransferase (HS 2-OST) and heparosan-N-sulfate-glucouronate 5-epimerase (HNSG-5epi).

2.1. Construction of pACYC184-MBP*-2OSTY94A(D69-N356) Plasmid

2.1.1. Construction of pMAL* Vector

The pMAL-c2X vector (New England BioLabs, cat. No. E8000S) was modified to replace the DNA fragment encoding peptide linker $S_3N_{10}$LGIEGRISEFGS with a DNA fragment encoding a C-terminus of MBP protein, wherein the glutamic acid residue at position 359 is replaced with an alanine residue (E359A), the lysine residue at position 362 is replaced with an alanine residue (K362A), and the aspartic acid residue at position 363 is replaced with an alanine residue (D363A) (Rob J. C. et al., Crystallization of a trimeric human T cell leukemia virus type 1 gp21 ectodomain fragment as a chimera with maltose-binding protein, Prot. Science, 1998, 7:1612-1619). In addition, restriction sites HindIII-BamHI-SacI-XhoI-NotI were introduced into the vector.

The PCR fragment containing a part of the C-terminus of MBP flanked by 5'-BglII and 3'-HindIII restriction sites was amplified using the primers P1 (SEQ ID NO: 7) and P2 (SEQ ID NO: 8), the pMAL-c2X plasmid as a template. The PCR product was ligated into the BglII/HindIII restriction sites of pMAL-c2X plasmid. Thus, pMAL* vector was constructed.

2.1.2. Construction of pMAL*-2OSTY94A(D69-N356) Plasmid

A DNA fragment (SEQ ID NO: 9) harboring a coding sequence (CDS) encoding a mutant HS 2-OST having the amino acid sequence shown in SEQ ID NO: 10 which corresponds to the polypeptide from the aspartic acid residue at position 69 (D69) to the asparagine residue at position 356 (N356) in the HS 2-OST native to *Cricetulus longicaudatus* (UniProtKB, accession No. 00889.1), wherein the tyrosine residue at position 94 is replaced with alanine residue (Y94A), was synthesized chemically by GeneArt® custom DNA synthesis (Thermo Fisher Scientific). The DNA fragment was digested using restrictases NotI and XhoI, and cloned into pMAL*/NotI-XhoI vector (Example 2.1.1). Thus, pMAL*-2OSTY94A(D69-N356) plasmid was constructed.

2.1.3. Construction of pACYC184-MBP*-2OSTY94A(D69-N356) Plasmid

The 3.6-kbp FspI-HindIII DNA fragment of pMAL*-2OST(D69-N356) plasmid was sub-cloned into EcoRV/HindIII restriction sites of pACYC184 cloning vector (GenBank/EMBL, accession No. X06403). Thus, pACYC184-MBP*-2OSTY94A(D69-N356) plasmid was constructed.

2.2. Construction of pSUMO-dreGlce(G70-N585) Plasmid

A DNA fragment (SEQ ID NO: 11) encoding N-tagged 6×His-SUMO peptide (SEQ ID NO: 12) derived from pETite™ N-His SUMO Kan Vector (Lucigen Corporation, 2905 Parmenter St, Middleton, WI53562 USA), which peptide is fused with (G70-N585) fragment of HNSG-5epi having the amino acid sequence shown in SEQ ID NO: 13 which corresponds to the polypeptide from the glycine residue at position 70 (G70) to the asparagine residue at position 585 (N585) in the HNSG-5epi native to *Danio rerio* (NCBI Reference Sequence: NP_998014.1), was synthesized chemically by GeneArt® custom DNA synthesis (Thermo Fisher Scientific). The DNA fragment was digested using restrictases NdeI and XhoI, cloned into pMAL*/NdeI-XhoI vector (Example 2.1.1). Thus, pSUMO-dreGlce(G70-N585) plasmid was constructed.

2.3. Construction of Δ2-5-Strains Harboring pACYC184-MBP*-2OSTY94A(D69-N356) and pSUMO-dreGlce(G70-N585) Plasmids The pACYC184-MBP*-2OSTY94A(D69-N356) and pSUMO-dreGlce(G70-N585) plasmids were introduced into Δ2-5-strains using standard electroporation procedure (0.1 cm cuvette (Bio-Rad); voltage, 2 kV; duration, 5 μs). First, the pSUMO-dreGlce(G70-N585) plasmid was introduced to construct Δ2-5/pSUMO-dreGlce(G70-N585) strains. Then, the pACYC184-MBP*-2OSTY94A(D69-N356) plasmid was introduced into Δ2-5/pSUMO-dreGlce(G70-N585) strains to construct the target Δ2-5-strains harboring two plasmids. The Δ2-5-strains harboring pACYC184-MBP*-2OSTY94A(D69-N356) and pSUMO-dreGlce(G70-N585) plasmids were referred as Δ2-5/pSUMO/pACYC184 strains.

2.4. Preparation of Soluble Fractions of Crude Cell Lysates of Δ2-5/pSUMO/pACYC184

The cell cultures of Δ2-5-strains harboring pACYC184-MBP*-2OSTY94A(D69-N356) and pSUMO-dreGlce(G70-N585) plasmids in a volume of 1.25 mL each, grown overnight in LB-broth containing ampicillin (200 mg/L) and chloramphenicol (30 mg/L), were inoculated into 50 mL of the LB-broth containing ampicillin (150 mg/L) and chloramphenicol (30 mg/L) in flasks, and then cultivated at 37° C. to $OD_{600}$ about 0.8. Then, synthesis of HS 2-OST and HNSG-5epi was induced by adding IPTG (isopropyl β-D-1-thiogalactopyranoside) to a final concentration of 0.5 mM. The cultivation was continued at 20° C. for 48 hours.

The resulting biomasses were harvested by centrifugation (5000 rpm), re-suspended in 0.3 mL of 50 mM MES (2-(N-morpholino) ethanesulfonic acid) solution (pH 7) and subjected to sonication for cells disruption. Insoluble fractions of crude cell lysates containing insoluble proteins were then precipitated by centrifugation (13000 rpm), re-suspended in 0.3 mL of a sample buffer (20 mM Tris-HCl, pH 6.8; 50 mM DTT (1,4-dithiothreitol), 0.1% (v/v) SDS, 30% (v/v) glycerol) and incubated at 95° C. for 10 min. Insoluble fractions was then precipitated again by centrifugation (13000 rpm). Obtained supernatants were used as insoluble proteins preparations. Soluble fractions of crude cell lysates (so-called supernatants) obtained as a result of the above procedure and containing soluble proteins, including proteins having heparan sulfate 2-O-sulfotransferase and heparosan-N-sulfate-glucouronate 5-epimerase activities were transferred into new vials and stored at 4° C. for up to 3-5 hours until the use. The average concentration of proteins in thus prepared soluble fractions of crude cell lysates was 20 mg/mL.

Figure 3A:
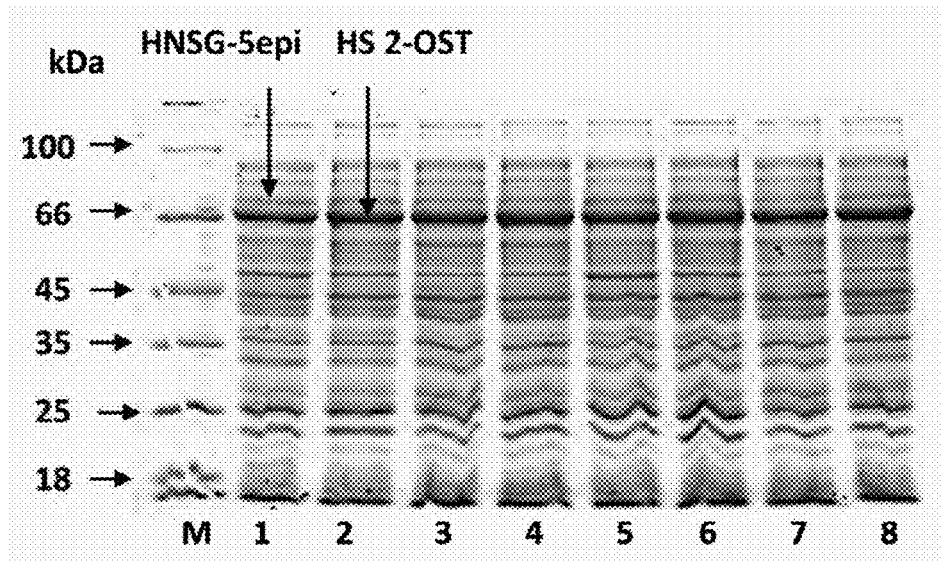
FIGS. 3A and 3B show the results of SDS-PAGE analysis of soluble and insoluble fractions of crude cell lysates of Δ2-5-strains harboring pACYC184-MBP*-2OSTY94A (D69-N356) and pSUMO-dreGlce(G70-N585) plasmids. Panel A—soluble fraction, panel B—insoluble fraction; lanes: M—marker of indicated molecular weights, 1 and 2—Δ2-strain, 3 and 4—Δ3-strain, 5 and 6—Δ4-strain, 7 and 8—Δ5-strain; HS 2-OST—heparan sulfate 2-O-sulfotransferase fused with MPB*N-tag, HNSG-5epi—heparosan-N-sulfate-glucouronate 5-epimerase fused with SUMO N-tag.
Figure 3B:
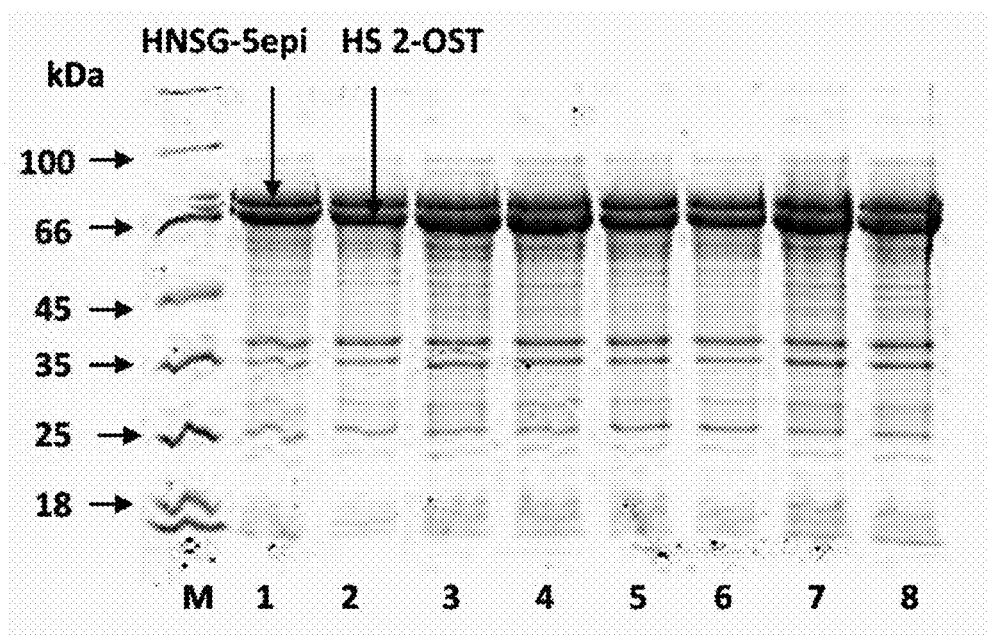

In order to analyze content of proteins in soluble and insoluble fractions of crude cell lysates of Δ2-5-strains harboring pACYC184-MBP*-2OSTY94A(D69-N356) and pSUMO-dreGlce(G70-N585) plasmids, 1 μL of each preparation was subjected to SDS-PAGE analysis (FIG. 3). As one can see from the FIG. 3, the absolute and relative quantity of HS 2-OST and HNSG-5epi in all analyzed crude cell lysates of the strains was the same.

2.5. 2—O-Sulfurylation of LMWHS Using PAPS as a Donor of Sulfo Group

2-O-Sulfurylation of LMWHS was performed in a reaction mixture of a total volume 100 μL containing: 50 mM MES, pH 7; 1 mM $MgCl_2$; 1% (v/v) Triton x 100; 1 mM $CaCl_2$); 1.2 mM PAPS; 1 mg/mL LMWHS (Auxiliary example); and 83 μL of soluble fraction of a crude cell lysate (Example 2.4). The negative (control) reaction contained the above components except for the lysate which was replaced with water. The reaction mixture was incubated at 30° C. for 48 hours. Then, a part of the reaction mixture was treated with heparinase I, II, and III (New England BioLabs, cat. No. P0735S, P0736S, P0737S). A reaction mixture in a total volume of 100 μL contained: 30 μL of the reaction mixture obtained after the incubation, L of heparinase buffer (New England BioLabs), heparinase I, II, and III (1 μL of each enzyme), and 60 μL of $H_2O$. The reaction mixture was incubated at 30° C. for 24 hours, and then analyzed using HPLC method for the presence and quantity of disaccharides NS (α-ΔUA-[1→4]-GlcNS) and NS2S (α-ΔUA-2S-[1→4]-GlcNS). Conditions of the HPLC analysis were as described in Example 1.4.

The results of 2-O-sulfurylation of LMWHS are shown in Table 4. As one can see from the Table 4, the 2-O-sulfurylation of LMWHS using PAPS as a donor of sulfo group was about 1.4 times more effective when the crude cell lysate of Δ5/pSUMO/pACYC184 strain having deleted cysQ, cpdB, and aphA genes was used as compared with the Δ2/pSUMO/pACYC184 strain.

Example 3. Enzymatic Sulfurylation of Low Molecular Weight Heparosan N-Sulfate in the Presence of pNPS The enzymatic sulfurylation of LMWHS was performed also in crude cell lysates of Δ2-5/pSUMO/pACYC184 strains containing pNPS and an aryl sulfotransferase using PAPS as a donor of sulfo group.

3.1. Expression and Purification of *Rattus norvegicus* Aryl Sulfotransferase 1A1

First, the pETDuet-N-Tag6×His-ST1A1 plasmid harboring the gene encoding ST1A1 native to *Rattus norvegicus* was constructed. A DNA fragment (SEQ ID NO: 14) containing the gene encoding aryl sulfotransferase 1A1 (abbreviated as "ST1A1", also known as "Sult1a1") native to *Rattus norvegicus* (NCBI Reference Sequence: NP_114022.1) was synthesized chemically by GeneArt® custom DNA synthesis (Thermo Fisher Scientific). The obtained DNA fragment was digested using restrictases EcoRI and HindIII and cloned into pETDuet-1/EcoRI-HindIII vector (Novagen). Thus, a gene encoding ST1Δ1 native to *Rattus norvegicus* fused with 6×His-tag was obtained.

Then, the 6×His-tagged ST1Δ1 was expressed and purified using immobilized metal ion affinity chromatography (IMAC) on a 1-mL HiTrap column (GE Healthcare). The standard procedures recommended by the manufacturer were applied.

3.2. 2—O-Sulfurylation of LMWHS in the Presence of pNPS

2-O-Sulfurylation of LMWHS was performed in a reaction mixture of a total volume 100 µL containing: 50 mM MES, pH 7; 1 mM $MgCl_2$; 1% (v/v) Triton x 100; 1 mM $CaCl_2$); 46 µM PAP; 10 mM pNPS; 1 mg/mL LMWHS (Auxiliary example); 4.75 µg ST1Δ1 (Example 3.1); and 74 µL of soluble fraction of a crude cell lysate (Example 2.4). The negative (control) reaction contained the above components except for the lysate which was replaced with water. Reaction mixture was incubated at 30° C. for 48 hours. Conditions of the treatment of the reaction mixture with heparinases and analysis of the obtained mixtures using HPLC were the same as described in Example 2.5.

The results of 2-O-sulfurylation of LMWHS in the presence of pNPS are shown in Table 5. As one can see from Table 5, the sulfurylation yield of LMWHS in the presence of pNPS using PAPS as a donor of sulfo group was 75% when the crude cell lysate of Δ5/pSUMO/pACYC184 strain having deleted cysQ, cpdB, and aphA genes was used, whereas the sulfurylated product of the LMWHS was not detected when the crude cell lysate of Δ2/pSUMO/pA-CYC184 strain was used. Also, the 2-O-sulfurylation of LMWHS in the presence of pNPS using PAPS as a donor of sulfo group was about 16 and 15 times higher when the crude cell lysate of Δ5/pSUMO/pACYC184 strain having deleted cysQ, cpdB, and aphA genes was used as compared with, respectively, Δ3/pSUMO/pACYC184 strain having deleted cysQ gene and Δ4/pSUMO/pACYC184 strain having deleted cysQ and cpdB genes.

Example 4. Enzymatic Sulfurylation of PAP Using pNPS as a Donor of Sulfo Group

4.1. Construction of pPlac-N-Tag6×his-ST1Δ1 Plasmid

To construct pPlac-N-Tag6×His-ST1Δ1 plasmid, a DNA fragment was obtained by PCR using the primers P3 (SEQ ID NO: 15) and P4 (SEQ ID NO: 16), and the pETDuet-N-Tag6×His-ST1Δ1 plasmid (Example 3.1) as a template. The obtained DNA fragment was ligated into the NdeI/HindIII sites of pMAL* plasmid (Example 2.1.1).

4.2. Construction of Δ2-5-Strains Harboring pPlac-N-Tag6×his-ST1Δ1 Plasmid

The pPlac-N-Tag6×His-ST1Δ1 plasmid was introduced into Δ2-5-strains (Example 1.2, Table 1) using standard electroporation procedure (0.1-cm cuvette (Bio-Rad); voltage, 2 kV; duration, 5 s). The Δ2-5-strains harboring pPlac-N-Tag6×His-ST1Δ1 plasmid were referred to as Δ2-5/pST1Δ1 strains.

4.3. Preparation of Soluble Fractions of Crude Cell Lysates of Δ2-5/pST1Δ1 Strains The cells of Δ2-5/pST1Δ1 strains, that were freshly made by growing for overnight on agar-plates, were inoculated into 5 mL of LB-broth containing ampicillin (200 mg/L) in 20 mL-test tube up to the initial $OD_{595}$ of 0.1 and cultivated at 37° C. to the final $OD_{595}$ of 1.2. Then, synthesis of N-Tag6×His-ST1Δ1 was induced by adding IPTG (isopropyl 3-D-1-thiogalactopyranoside) to a final concentration of 1 mM. The cultivation was continued at 25° C. for 16 hours. The resulting biomass was harvested by centrifugation at 4° C. for 10 minutes at 3.3 rcf (relative centrifugal force), washed twice with 25 mL of 0.9% NaCl solution, and frozen at −20° C. until used.

Thawed cells pellet was re-suspended in 0.5 mL of buffer (100 mM Tris-HCl, 10% (v/v) glycerol, pH 7.4), and cells were disrupted by sonication. Cells debris was removed by centrifugation at 13000 rpm for about 20 minutes. Resulting crude cell lysates were used as ST1Δ1 protein preparations.

4.4. Sulfurylation of PAP Using pNPS as a Donor of Sulfo Group

Figure 4:
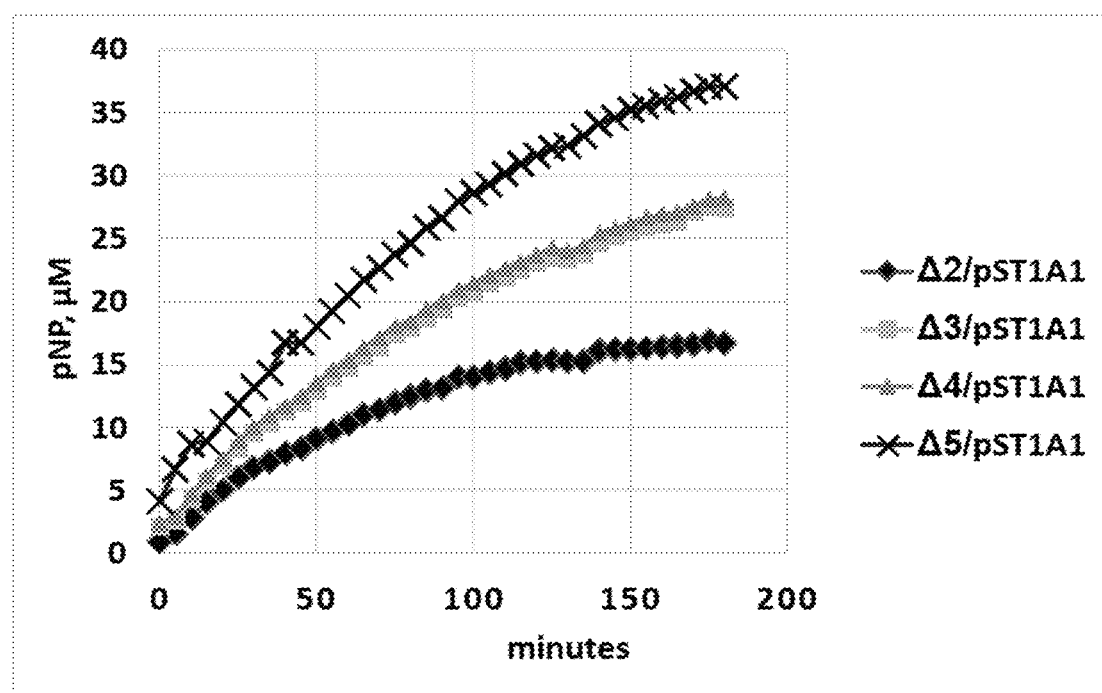
FIG. 4 shows the kinetic curves for the accumulation of pNP in reaction mixtures upon the sulfurylation of PAP using crude cell lysates of Δ2-Δ5/pST1Δ1 strains and pNPS as a donor of sulfo group.

Each reaction mixture of a total volume 100 µL contained: 50 mM Tris-HCl, pH 7; 230 µM PAP; 1 mM pNPS; 10% (v/v) glycerol; 0.1 mg/mL of a crude cell lysate of Δ2-5/pST1Δ1 strains. The mixtures were prepared in a standard 96-well plate. The reactions were initiated by adding the PAP. Reaction mixtures were incubated at 30° C. for 3 hours in MultiskanGo (Thermo Scientific). The $OD_{405}$ was measured every 5 minutes for all used wells, such that the kinetics of pNP synthesis was obtained (FIG. 4). Absolute pNP concentration was determined using calibration curve that was obtained as the dependence of $OD_{405}$ on the concentration of pNP. The accumulated amount of PAPS in reaction mixtures (in molar ratio) was assumed to be equal to the accumulated amount of pNP in the view of the equation: PAP+pNPS=PAPS+pNP.

As one can see from the obtained experimental data (FIG. 4), the highest sulfurylation yield of PAP was observed when the crude cell lysate of Δ5/pST1Δ1 strain having deleted cysQ, cpdB, and aphA genes was used. The accumulation yield (in M) of PAPS in the crude cell lysate of Δ5/pST1Δ1 strain was about two times higher as compared with that yield in the crude cell lysate of Δ2/pST1Δ1 strain not having the deleted cysQ, cpdB, and aphA genes.

Auxiliary Example. Preparation of Low Molecular Weight Heparosan N-Sulfate (LMWHS)

(1) Preparation of Heparosan (1.1) Heparosan Fermentation

A culture solution containing heparosan was obtained using the heparosan-producing bacterium (*Escherichia coli* BL21 (DE3)/pVK9-kfiABCD strain) and the culture conditions described in Example 1 of WO2015/050184.

(1.2) Purification of Heparosan

A culture supernatant was collected from the culture solution by centrifugation. In order to remove medium ingredients, 1 mL of the culture supernatant was washed with Milli-Q water using a UF membrane, and concentrated to 250 µL. To 250 µL of the solution concentrated with the UF membrane, 500 µL of 100% ethanol was added, and heparosan was precipitated by centrifugation. The resulting precipitate was dried in air to obtain heparosan. Also, from the remaining culture supernatant, heparosan was purified using the same procedure. Total 10 g of heparosan was obtained.

(2) N-Deacetylation of Heparosan

A) To 1.22 g of the heparosan, 61 mL of hydrazine·$H_2O$ and 4.7 mL of 1N sulfuric acid were added, and after replacing the gas phase with nitrogen, the mixture was heated to 100° C. and reacted for 4.75 hours.

B) After stopping the reaction by ice cooling, 61 mL of 16% NaCl aqueous solution and 610 mL of MeOH were added and the mixture was centrifuged. The supernatant was removed. The resulting precipitate was dissolved in 50 mL of $H_2O$, and was then desalted and concentrated using Amicon UF membrane (3 kDa).

C) To the resulting concentrated solution, the twice volume of $H_2O$ and the equivalent volume of 1 M $NaHCO_3$ were added, and then, 0.2 M $I_2$/0.4 M KI solution was dripped until coloring yellow. Subsequently, hydrazine·$H_2O$ was dripped to reduce the excessive iodine to iodine ion, and then the solution was desalted and concentrated using Amicon UF membrane (3 kDa) again. The concentrated solution was dried under reduced pressure to obtain N-deacetylated heparosan. The residual rate of the acetyl group in the obtained N-deacetylated heparosan was 14.9% (described later).

(3) Depolymerization of N-Deacetylated Heparosan (3.1) Preparation of Heparinase III (3.1.1) Construction of Expression Plasmid Harboring hepC Gene Native to *Flavobacterium heparinum*

The hepC gene encoding heparinase III native to *Flavobacterium heparinum* was cloned into a pMIV-Pn1p0 vector (US Patent Application publication No. 20050196846) to construct the hepC gene expression plasmid pMIV-Pn1p0-hepC. The pMIV-Pn1p0-ter includes a potent n1p0 promoter (Pn1p0) and a rrnB terminator, and can function as an expression unit by inserting an objective gene between the promoter and the terminator. "Pn1p0" represents a promoter for the wild-type nlpD gene native to *Escherichia coli* K-12.

Details for the construction of the expression plasmid is shown below. A DNA fragment that includes about 300 bp of a promoter region (Pn1p0) for the nlpD gene was obtained by PCR with chromosomal DNA from *Escherichia coli* MG1655 as a template using primer P5 (SEQ ID NO: 17) and primer P6 (SEQ ID NO: 18). Sites for restriction enzymes SalI and PaeI have been designed in each 5' terminus of these primers. PCR cycles were as follows: first, 95° C. for 3 minutes, then two cycles of 95° C. for 60 seconds, 50° C. for 30 seconds and 72° C. for 40 seconds, subsequently 25 cycles of 94° C. for 20 seconds, 55° C. for 20 seconds and 72° C. for 15 seconds, and finally 72° C. for 5 minutes. A resulting DNA fragment was treated with SalI and PaeI, and inserted into the SalI-PaeI site of pMIV-5JS (Japanese Patent Application Publication No. 2008-99668) to obtain plasmid pMIV-Pn1p0. The nucleotide sequence of the PaeI-SalI fragment of the Pn1p0 promoter inserted into this pMIV-Pn1p0 plasmid is as shown in SEQ ID NO: 19.

Subsequently, the DNA fragment (SEQ ID NO: 20) that includes about 300 bp of a terminator region of the rrnB gene was obtained by PCR with chromosomal DNA from MG1655 as a template using primer P7 (SEQ ID NO: 21) and primer P8 (SEQ ID NO: 22). Sites of restriction enzymes XbaI and BamHI have been designed at each 5' terminus of these primers. The PCR cycles were as follows: first, 95° C. for 3 minutes, then two cycles of 95° C. for 60 seconds, 50° C. for 30 seconds and 72° C. for 40 seconds, subsequently 25 cycles of 94° C. for 20 seconds, 59° C. for 20 seconds and 72° C. for 15 seconds, and finally 72° C. for 5 minutes. A resulting fragment was treated with XbaI and BamHI, and inserted into the XbaI-BamHI site of pMIV-Pn1p0 to obtain plasmid pMIV-Pn1p0-ter.

Subsequently, a DNA chain that includes ORF of the hepC gene native to *Flavobacterium heparinum* (ATCC 13125; Su H. et al., Appl. Environ. Microbiol., 1996, 62:2723-2734) was artificially synthesized. A DNA fragment of the hepC gene was amplified by PCR with this DNA chain as a template using primer P9 (SEQ ID NO: 23) and primer P10 (SEQ ID NO: 24). The PCR was performed using PrimeStar polymerase (TaKaRa) in the reaction composition described in the protocol. The PCR cycle was as follows: first, 94° C. for 5 minutes, then 30 cycles of 98° C. for 5 seconds, 55° C. for 10 seconds and 72° C. for 8 minutes, and finally keeping at 4° C. Also, a DNA fragment of pMIV-Pn1p0 was obtained by PCR with pMIV-Pn1p0 as a template DNA using oligonucleotides of a primer P11 (SEQ ID NO: 25) and a primer P12 (SEQ ID NO: 26) as primers. PCR was performed using PrimeStar polymerase (TaKaRa) and the reaction composition described in the protocol. The PCR cycle was as follows: first, 94° C. for 5 minutes, then 30 cycles of 98° C. for 5 seconds, 55° C. for 10 seconds and 72° C. for 6 minutes, and finally keeping at 4° C. Resulting both DNA fragments were ligated using In-Fusion (registered trademark) HD cloning kit (Clontech) to construct the hepC gene expression plasmid pMIV-Pn1p0-hepC. A nucleotide sequence of the cloned hepC gene and an amino acid sequence of heparinase III (HepC) encoded by it are shown in SEQ ID NOs: 27 and 28, respectively.

(3.1.2) Construction of *Escherichia coli* BL21 (DE3) Strain Expressing hepC Gene and Preparation of Heparinase III Enzyme Solution The hepC gene expression plasmid pMIV-Pn1p0-hepC was introduced into *Escherichia coli* BL21 (DE3) strain (Life Technologies) by electroporation (Cell; 80 µL, 200 Ω, 25 µF, 1.8 kV, cuvette; 0.1 mL) to obtain *Escherichia coli* BL21 (DE3)/pMIV-Pn1p0-hepC strain as a heparinase III-producing strain. This strain was pre-cultured in 25 µg/mL chloramphenicol-added LB medium at 37° C. overnight. Subsequently, the culture solution was inoculated to 300 mL LB medium in a Sakaguchi flask at a final concentration of 2% (v/v). The cultivation with shaking was performed at 37° C. for 4 hours, and the cultivation was stopped. After centrifugation, the microbial cells were washed twice with 0.85% NaCl, and suspended in 30 mL of 50 mM HEPES buffer (pH 7.0). The suspension was subjected to sonication disruption to disrupt the microbial cells. The disrupted microbial cell solution was centrifuged to prepare a heparinase III enzyme solution as a supernatant (cell free extract solution)

(3.2) Depolymerization of N-Deacetylated Heparosan Using Heparinase III

The 1 g of N-deacetylated heparosan with an N-acetyl group residual rate of 14.9% obtained in (2) and 2 mL of 31.3 mIU/µL heparinase III solution were dissolved in 100 mL of Tris buffer solution (pH 8.0) containing 100 mM NaCl and 1.5 mM CaCl$_2$), and reacted at 37° C. for 5.3 hours. To the reaction solution, 100 mL of 16% NaCl aqueous solution and 900 mL of EtOH were added and mixed, and were centrifuged to remove a supernatant and obtain depolymerized N-deacetylated heparosan.

(4) N-Sulfation of Depolymerized N-Deacetylated Heparosan

A) The 1 g of the depolymerized N-deacetylated heparosan obtained in (3) was dissolved in 50 mL of Milli-Q water, and 50 mL of an aqueous solution of 20 mg/mL NaHCO$_3$/20 mg/mL trimethylamine-SO$_3$ was added thereto, and the mixture was reacted at 55° C. overnight.

B) To the mixture, 1 L of EtOH was added, which was then centrifuged to remove a supernatant to obtain N-sulfated depolymerized heparosan.

C) The obtained N-sulfated depolymerized heparosan was dissolved in Milli-Q water up to 500 µL, and the disaccharide analysis was performed to calculate a yield relative to N-deacetylated heparosan. Also, it was subjected to GPC to calculate a molecular weight distribution. The procedures are shown below.

<Disaccharide Analysis>

The disaccharide analysis of N-sulfated depolymerized heparosan was performed according to the conditions previously reported (T. Imanari et al., "High-performance liquid chromatographic analysis of glycosaminoglycan-derived oligosaccharides", J. Chromatogr. A, 1996, 720:275-293). That is, an amount of each constituent disaccharide was quantified by decomposing N-sulfated depolymerized heparosan into unsaturated disaccharides using heparinases II and III and analyzing each decomposed product by HPLC.

Likewise, the disaccharide analysis of N-deacetylated heparosan was performed. The disaccharide analysis of N-deacetylated heparosan was performed after N-deacetylated heparosan was N-sulfated. That is, the amount of each constituent disaccharide was quantified by N-sulfating N-deacetylated heparosan, subsequently decomposing it into unsaturated disaccharides using heparinases II and III, and analyzing each decomposed product by HPLC. The N-sulfation of N-deacetylated heparosan was performed as was the case with the N-sulfation of depolymerized N-deacetylated heparosan.

The disaccharide analysis was specifically performed by the following procedure.

1) The 0.2 U of heparinase II (Sigma), 0.02 to 0.03 mIU of heparinase III, 5 µg of a polysaccharide sample, and 10 µL of buffer for enzymatic digestion (100 mM CH$_3$COONa, 10 mM (CH$_3$COO)$_2$Ca, pH 7.0) were mixed and diluted with Milli-Q water up to 100 µL of measured volume to use as a reaction solution.

2) The reaction solution was kept at 37° C. for 16 hours or longer, and subsequently boiled at 100° C. for 2 minutes to stop the reaction.

3) Impurities were removed through 0.45 m filter to obtain a solution, which was then used as a sample for the disaccharide analysis.

4) The analysis was performed using a column of Inertsil ODS-3 150 mm×2.1 mm with 5 m particle size under the conditions of temperature at 50° C., a flow date of 0.25 mL/min and a detection wavelength of 230 nm, and using an eluent composition of 4% acetonitrile and 1.2 mM tributylamine as solution A and 4% acetonitrile and 0.1 M CsCl as solution B with a gradient from 1 to 90% of solution B.

The yield was calculated from the sum of the amounts of constituent disaccharides produced from each polysaccharide sample. That is, the yield was calculated as a percentage (molar ratio) of a total amount of disaccharides produced from N-sulfated depolymerized heparosan relative to a total amount of disaccharides produced from N-deacetylated heparosan. Also, at that time, it was confirmed that 99% or more of amino groups produced by N-acetylation was N-sulfated in the obtained N-sulfated depolymerized heparosan.

Also, the residual rate of the N-acetyl groups in N-deacetylated heparosan was calculated based on the amount of each constituent disaccharide produced from N-deacetylated heparosan. That is, the residual rate of the acetyl group was calculated as a percentage (molar ratio) of the amount of disaccharides having the acetyl group relative to the total amount of disaccharides. The residual rate of the acetyl groups was 14.9%.

<GPC Analysis>

N-sulfated depolymerized heparosan and heparan sulfate (dissolved at 1 mg/mL in Milli-Q water) was subjected to gel filtration by HPLC (GPC analysis). GS520 (Shodex, Asahipak GS-520HQ, 7.5 mm×300 mm, particle size of 7 m) was used as a column, an aqueous solution of 100 mM potassium dihydrogen phosphate was used as an eluent, and the analysis was performed at a flow rate of 0.6 mL/min, at a column temperature of 40° C., and at a detection wavelength of 200 nm. Average molecular weights (Mn and Mw) were calculated using a molecular weight marker set of pullulan (Shodex, STANDARD P-82, molecular weight range from 5900 to 708000) as a standard.

INDUSTRIAL APPLICABILITY

The method of the present invention is useful for the enzymatic production of O- and N-sulfated derivatives of alcohols and amines. In particular, the method is suitable for the A production of heparin and heparan sulfate.

TABLE 1

| | Constructed strains. |
|---|---|
| Strain | Genotype |
| Δ0 | Origami ® 2 |
| Δ2 | Origami ® 2 (ΔptrA ΔhslU) |
| Δ3 | Origami ® 2 (ΔptrA ΔhslU ΔcysQ) |
| Δ4 | Origami ® 2 (ΔptrA ΔhslU ΔcysQ ΔcpdB) |
| Δ5 | Origami ® 2 (ΔptrA ΔhslU ΔcysQ ΔcpdB ΔaphA) |

TABLE 2

| | Stability of PAP. | | | | |
|---|---|---|---|---|---|
| Time, | Concentration of PAP (mg/L) | | | | |
| hours | control | Δ2 | Δ3 | Δ4 | Δ5 |
| 0 | 0.4 | 0.25 | 0.4 | 0.4 | 0.4 |
| 1 | NA | <0.005 | 0.3 | 0.3 | 0.4 |
| 2 | | | 0.2 | 0.3 | 0.3 |

TABLE 2-continued

Stability of PAP.

| Time, hours | Concentration of PAP (mg/L) | | | | |
|---|---|---|---|---|---|
| | control | Δ2 | Δ3 | Δ4 | Δ5 |
| 4 | | | 0.1 | 0.3 | 0.3 |
| 22 | 0.4 | | <0.005 | 0.1 | 0.2 |

NA: not analyzed

TABLE 3

Stability of PAPS.

| Time, hours | Concentration of PAPS (mg/L) | | | | |
|---|---|---|---|---|---|
| | control | Δ2 | Δ3 | Δ4 | Δ5 |
| 0 | 0.4 | 0.4 | 0.4 | 0.4 | 0.4 |
| 1 | NA | 0.3 | 0.4 | 0.4 | 0.4 |
| 2 | | 0.3 | 0.3 | 0.3 | 0.3 |
| 4 | | 0.2 | 0.3 | 0.3 | 0.3 |
| 22 | 0.3 | 0.006 | 0.09 | 0.1 | 0.2 |

NA: not analyzed

TABLE 4

2-O-Sulfurylation of LMWHS using PAPS.

| Strain [1] | Disaccharide [2] | | | Sulfurylation yield, % [4] |
|---|---|---|---|---|
| | NS, g/L | NS2S, g/L | Sum, g/L [3] | |
| control | 0.251 | <0.005 | 0.251 | <2 |
| Δ2* | 0.104 | 0.147 | 0.251 | 59 |
| Δ3* | 0.074 | 0.170 | 0.244 | 70 |
| Δ4* | 0.093 | 0.165 | 0.258 | 64 |
| Δ5* | 0.043 | 0.185 | 0.228 | 81 |

[1] Strain:
Δ2*: Δ2/pSUMO/pACYC184,
Δ3*: Δ3/pSUMO/pACYC184,
Δ4*: Δ4/pSUMO/pACYC184,
Δ5*: Δ5/pSUMO/pACYC184.
[2] Disaccharide:
NS: α-ΔUA-[1→4]-GlcNS, NS2S: α-ΔUA-2S-[1→4]-GlcNS, wherein ΔUA means 4-deoxy-L-threo-hex-4-enopyranosyluronic acid and GlcNS means N-sulfo-D-glucosamine.
[3] Sum: NS + NS2S. The cumulative quantity of NS and NS2S was less than the amount of the initial LMWHS, because the effectiveness of cleavage of the LMWHS using heparinase I, II, and III was about 30%.
[4] Sulfurylation yield: NS2S/(NS + NS2S). It does not depend on the effectiveness of cleavage of LMWHS.

TABLE 5

2-O-Sulfurylation of LMWHS in the presence of pNPS.

| Strain [1] | Disaccharide [2] | | | Sulfurylation yield, % [4] |
|---|---|---|---|---|
| | NS, g/L | NS2S, g/L | Sum, g/L [3] | |
| control | 0.224 | <0.005 | 0.224 | <2 |
| Δ2* | 0.224 | <0.005 | 0.224 | <2 |
| Δ3* | 0.218 | 0.010 | 0.228 | 4.6 |
| Δ4* | 0.212 | 0.010 | 0.223 | 4.9 |
| Δ5* | 0.066 | 0.198 | 0.264 | 75 |

[1], [2], [3], and [4] - see explanations to the Table 4.

The invention claimed is:

1. A method for enzymatic sulfurylation of a substrate or for producing a sulfated derivative of a substrate comprising:
   (i) reacting the substrate with 3'-phosphoadenosine-5'-phosphosulfate in a medium containing a bacterium belonging to the genus *Escherichia* to produce a sulfated derivative of said substrate, and
   (ii) collecting the sulfated derivative from the medium;
   wherein said substrate has a chemical group selected from the group consisting of a hydroxyl group, an amino group, and combinations thereof; and
   wherein said bacterium has been modified
   (A) to produce, at least, a protein having sulfotransferase activity, and
   (B) to attenuate expression of an aphA gene or a cysQ gene.

2. The method according to claim 1, wherein said bacterium modified to attenuate expression of the aphA gene has been modified further to attenuate expression of the cysQ gene or a cpdB gene, or a combination thereof.

3. The method according to claim 1, wherein said bacterium modified to attenuate expression of the cysQ gene has been modified further to attenuate expression of the aphA gene or a cpdB gene, or a combination thereof.

4. The method according to claim 1, wherein said protein having sulfotransferase activity is selected from the group consisting of a protein having O-sulfotransferase activity, a protein having N-sulfotransferase activity, and a protein having N-deacetylase/N-sulfotransferase activity.

5. The method according to claim 4, wherein said protein having O-sulfotransferase activity is selected from the group consisting of a protein having heparan sulfate 2-O-sulfotransferase activity, a protein having heparan sulfate 3-O-sulfotransferase activity, a protein having heparan sulfate 6-O-sulfotransferase activity, and combinations thereof.

6. The method according to claim 1, wherein said bacterium has been modified further to produce a protein having heparosan-N-sulfate-glucouronate 5-epimerase activity.

7. The method according to claim 1, wherein said bacterium has been modified further to produce a protein having 3'-phosphoadenosine-5'-phosphosulfate-sulfotransferase activity.

8. The method according to claim 7, wherein said medium contains the protein having 3'-phosphoadenosine-5'-phosphosulfate-sulfotransferase activity.

9. The method according to claim 1, wherein said substrate is selected from the group consisting of heparosan, heparan sulfate, and heparin.

10. The method according to claim 1, wherein said sulfated derivative is selected from the group consisting of heparin, heparan sulfate, chondroitin sulfate, choline sulfate, and dermatan sulfate.

11. The method according to claim 1, wherein said bacterium is *Escherichia coli*.

12. The method according to claim 1, wherein said substrate has at least one hydroxyl group.

13. The method according to claim 1, wherein said substrate is a saccharide compound having at least one hydroxyl group.

14. The method according to claim 13, wherein said substrate is selected from the group consisting of heparosan, heparan sulfate, and heparin.

15. The method according to claim 13, wherein said sulfated derivative is selected from the group consisting of heparin, heparan sulfate, chondroitin sulfate, choline sulfate, and dermatan sulfate.

16. The method according to claim 1, wherein said protein having sulfotransferase activity is a protein having O-sulfotransferase activity.

17. The method according to claim 16, wherein said protein having O-sulfotransferase activity is a protein having heparan sulfate 2-O-sulfotransferase activity.

\* \* \* \* \*

SEQUENCE LISTING

<160> NUMBER OF SEQ ID NOS: 28

<210> SEQ ID NO 1
<211> LENGTH: 714
<212> TYPE: DNA
<213> ORGANISM: Escherichia coli

<400> SEQUENCE: 1

```
atgcgcaaga tcacacaggc aatcagtgcc gtttgcttat tgttcgctct aaacagttcc      60
gctgttgccc tggcctcatc tccttcaccg cttaaccctg ggactaacgt tgccaggctt     120
gctgaacagg cacccattca ttgggtttcg gtcgcacaaa ttgaaaatag cctcgcaggg     180
cgtccgccaa tggcggtggg gtttgatatc gatgacacgg tactttttc cagtccgggc     240 ttctggcgcg gcaaaaaaac cttctcgcca gaaagcgaag attatctgaa aaatcctgtg     300
ttctgggaaa aaatgaacaa tggctgggat gaattcagca ttccaaaaga ggtcgctcgc     360
cagctgattg atatgcatgt acgccgcggt gacgcgatct tctttgtgac tggtcgtagc     420
ccgacgaaaa cagaaacggt ttcaaaaacg ctggcggata attttcatat tcctgccacc     480
aacatgaatc cggtgatctt tgcggggcgat aaaccagggc aaaatacaaa atcgcaatgg     540
ctgcaggata aaaatatccg aatttttat ggcgattctg ataatgatat taccgccgca     600
cgcgatgtcg gcgctcgtgg tatccgcatt ctgcgcgcct ccaactctac ctacaaaccc     660
ttgccacaag cgggtgcgtt tggtgaagag gtgatcgtca attcagaata ctga           714
```

```
<210> SEQ ID NO 2
<211> LENGTH: 237
<212> TYPE: PRT
<213> ORGANISM: Escherichia coli

<400> SEQUENCE: 2

Met Arg Lys Ile Thr Gln Ala Ile Ser Ala Val Cys Leu Leu Phe Ala
1               5                   10                  15

Leu Asn Ser Ser Ala Val Ala Leu Ala Ser Ser Pro Ser Pro Leu Asn
            20                  25                  30

Pro Gly Thr Asn Val Ala Arg Leu Ala Glu Gln Ala Pro Ile His Trp
        35                  40                  45

Val Ser Val Ala Gln Ile Glu Asn Ser Leu Ala Gly Arg Pro Pro Met
    50                  55                  60

Ala Val Gly Phe Asp Ile Asp Asp Thr Val Leu Phe Ser Ser Pro Gly
65                  70                  75                  80

Phe Trp Arg Gly Lys Lys Thr Phe Ser Pro Glu Ser Glu Asp Tyr Leu
                85                  90                  95

Lys Asn Pro Val Phe Trp Glu Lys Met Asn Asn Gly Trp Asp Glu Phe
            100                 105                 110

Ser Ile Pro Lys Glu Val Ala Arg Gln Leu Ile Asp Met His Val Arg
        115                 120                 125

Arg Gly Asp Ala Ile Phe Phe Val Thr Gly Arg Ser Pro Thr Lys Thr
    130                 135                 140

Glu Thr Val Ser Lys Thr Leu Ala Asp Asn Phe His Ile Pro Ala Thr
145                 150                 155                 160

Asn Met Asn Pro Val Ile Phe Ala Gly Asp Lys Pro Gly Gln Asn Thr
                165                 170                 175

Lys Ser Gln Trp Leu Gln Asp Lys Asn Ile Arg Ile Phe Tyr Gly Asp
            180                 185                 190

Ser Asp Asn Asp Ile Thr Ala Ala Arg Asp Val Gly Ala Arg Gly Ile
        195                 200                 205

Arg Ile Leu Arg Ala Ser Asn Ser Thr Tyr Lys Pro Leu Pro Gln Ala
    210                 215                 220

Gly Ala Phe Gly Glu Glu Val Ile Val Asn Ser Glu Tyr
225                 230                 235

<210> SEQ ID NO 3
<211> LENGTH: 741
<212> TYPE: DNA
<213> ORGANISM: Escherichia coli

<400> SEQUENCE: 3
atgttagatc aagtatgcca gcttgcacgg aatgcaggcg atgccattat gcaggtctac      60
gacgggacga aaccgatgga cgtcgtcagc aaagcggaca attctccggt aacggcagcg     120
gatattgccg ctcacaccgt tatcatggac ggtttacgta cgctgacacc ggatgttccg     180
gtcctttctg aagaagatcc tcccggttgg gaagtccgtc agcactggca gcgttactgg     240
ctggtagacc cgctggatgg tactaaagag tttattaaac gtaatggcga attcaccgtt     300
aacattgcgc tcattgacca tgcaaaccg attttaggcg tggtgtatgc gccggtaatg     360
aacgtaatgt acagcgcggc agaaggcaaa gcgtggaaag aagagtgcgg tgtgcgcaag     420
cagattcagg tccgcgatgc gcgcccgccg ctggtggtga tcagccgttc ccatgcggat     480
gcggagctga aagagtatct gcaacagctt ggcgaacatc agaccacgtc catcggctct     540
tcgctgaaat tctgcctggt ggcggaagga caggcgcagc tgtacccgcg cttcggacca     600
```

```
acgaatattt gggacaccgc cgctggacat gctgtagctg cagctgccgg agcgcacgtt    660
cacgactggc agggtaaacc gctggattac actccgcgtg agtcgttcct gaatccgggg    720
ttcagagtgt ctatttacta a                                              741
```

<210> SEQ ID NO 4
<211> LENGTH: 246
<212> TYPE: PRT
<213> ORGANISM: Escherichia coli

<400> SEQUENCE: 4

```
Met Leu Asp Gln Val Cys Gln Leu Ala Arg Asn Ala Gly Asp Ala Ile
1               5                   10                  15

Met Gln Val Tyr Asp Gly Thr Lys Pro Met Asp Val Val Ser Lys Ala
            20                  25                  30

Asp Asn Ser Pro Val Thr Ala Ala Asp Ile Ala Ala His Thr Val Ile
        35                  40                  45

Met Asp Gly Leu Arg Thr Leu Thr Pro Asp Val Pro Val Leu Ser Glu
    50                  55                  60

Glu Asp Pro Pro Gly Trp Glu Val Arg Gln His Trp Gln Arg Tyr Trp
65                  70                  75                  80

Leu Val Asp Pro Leu Asp Gly Thr Lys Glu Phe Ile Lys Arg Asn Gly
                85                  90                  95

Glu Phe Thr Val Asn Ile Ala Leu Ile Asp His Gly Lys Pro Ile Leu
            100                 105                 110

Gly Val Val Tyr Ala Pro Val Met Asn Val Met Tyr Ser Ala Ala Glu
        115                 120                 125

Gly Lys Ala Trp Lys Glu Glu Cys Gly Val Arg Lys Gln Ile Gln Val
    130                 135                 140

Arg Asp Ala Arg Pro Pro Leu Val Val Ile Ser Arg Ser His Ala Asp
145                 150                 155                 160

Ala Glu Leu Lys Glu Tyr Leu Gln Gln Leu Gly Glu His Gln Thr Thr
                165                 170                 175

Ser Ile Gly Ser Ser Leu Lys Phe Cys Leu Val Ala Glu Gly Gln Ala
            180                 185                 190

Gln Leu Tyr Pro Arg Phe Gly Pro Thr Asn Ile Trp Asp Thr Ala Ala
        195                 200                 205

Gly His Ala Val Ala Ala Ala Gly Ala His Val His Asp Trp Gln
    210                 215                 220

Gly Lys Pro Leu Asp Tyr Thr Pro Arg Glu Ser Phe Leu Asn Pro Gly
225                 230                 235                 240

Phe Arg Val Ser Ile Tyr
                245
```

<210> SEQ ID NO 5
<211> LENGTH: 1944
<212> TYPE: DNA
<213> ORGANISM: Escherichia coli

<400> SEQUENCE: 5

```
atgattaagt ttagcgcaac gctcctggcc acgctgattg ccgccagtgt gaatgcagcg    60
acggtcgatc tgcgtatcat ggaaaccact gatctgcata gcaacatgat ggatttcgat    120
tattacaaag acaccgccac ggaaaaattc ggactggtac gtacggcaag cctgattaac    180
gatgcccgca atgaagtgaa aaacagcgta ctggttgata cggcgatttt gattcagggg    240
```

```
agtccgctgg ccgattacat gtcggcgaaa ggattaaaag caggtgatat tcacccggtc    300
tataaggcat taaatacgct ggactatacc gtcggaacgc ttggcaacca cgagtttaac    360
tacggtctgg attacctgaa aaatgcgctg gcaggagcga aattccctta tgtaaatgcc    420
aacgtcattg acgccagaac caaacagcca atgtttacac cgtatttaat taaagacacc    480
gaagtggtcg ataaagacgg aaaaaaacag acgctgaaga ttggctatat tggcgtcgtg    540
ccaccacaaa tcatgggctg ggataaagct aatttatccg ggaaagtgac ggtgaatgat    600
attaccgaaa ccgtgcgcaa atacgtgcct gaaatgcgcg agaaaggtgc cgatgttgtt    660
gtcgttctgg cacattccgg gctatctgcc gatccgtata agtgatggc ggaaaactca    720 gtttattacc tcagtgaaat tccgggcgtt aacgccatta tgtttggcca tgctcacgcc    780
gttttcccag gtaaagattt tgctgatatc gaaggggctg atatcgccaa aggcacgctg    840
aatggtgttc cggcggtaat gccaggcatg tggggcgatc atcttggtgt ggtcgactta    900
caactcagta atgacagcgg taatggcag gtgacgcagg cgaaagcgga agcacgaccg    960
atttacgaca tcgctaataa aaaatccctc gcggcggaag acagcaagct ggtagaaaca   1020
ctcaaagccg atcacgatgc cacacgccag ttcgtcagca agccaatcgg taaatctgcc   1080
gacaatatgt atagctatct ggcgctggtg caggacgatc cgaccgtgca ggtggtgaac   1140
aacgcgcaaa aagcgtatgt cgagcattac attcagggcg atccggatct ggcaaaactg   1200
ccggtgcttt cagctgccgc accgtttaaa gtcgtggtc gcaaaaatga cccggcaagc   1260
tatgtggagg tggaaaaagg ccagttgacc ttccgtaatg ccgccgatct ttatctctat   1320
cccaatacgc tgattgtggt gaaagccagc ggtaaagagg tgaaagagtg gctggagtgc   1380
tccgcgggac agtttaacca gattgatccc aacagcacga aaccacagtc actcatcaac   1440
tgggatggtt tccgcactta taactttgat gttattgatg tgtgaatta tcagattgat   1500 gttacccagc ccgcccgtta tgacggcgag tgccagatga ttaatgccaa tgcggaaagg   1560
attaagaacc tgacctttaa tggcaagccg attgatccga acgccatgtt cctggttgcc   1620
accaataact atcgcgctta cggcggcaaa tttgccggta cgggcgacag ccatatcgct   1680
tttgcttcac cggatgagaa ccgctcggtg ctggcagcgt ggattgctga tgagtcgaaa   1740
cgtgcggggg aaattcaccc ggcggcagat aacaactggc gtttagcacc gatagctggc   1800
gataagaaac tggatatccg tttcgaaacc tctccgtcag ataaagccgc agcgtttatt   1860
aaagagaaag ggcagtatcc gatgaataaa gtcgcgaccg atgatatcgg gtttgcgatt   1920
tatcaggtgg atttgagtaa gtaa                                          1944
```

<210> SEQ ID NO 6  
<211> LENGTH: 647  
<212> TYPE: PRT  
<213> ORGANISM: Escherichia coli

<400> SEQUENCE: 6

```
Met Ile Lys Phe Ser Ala Thr Leu Leu Ala Thr Leu Ile Ala Ala Ser
 1               5                  10                  15

Val Asn Ala Ala Thr Val Asp Leu Arg Ile Met Glu Thr Thr Asp Leu
                20                  25                  30

His Ser Asn Met Met Asp Phe Asp Tyr Tyr Lys Asp Thr Ala Thr Glu
            35                  40                  45

Lys Phe Gly Leu Val Arg Thr Ala Ser Leu Ile Asn Asp Ala Arg Asn
        50                  55                  60

Glu Val Lys Asn Ser Val Leu Val Asp Asn Gly Asp Leu Ile Gln Gly
```

-continued

```
              65                  70                  75                  80
        Ser Pro Leu Ala Asp Tyr Met Ser Ala Lys Gly Leu Lys Ala Gly Asp
                         85                  90                  95
        Ile His Pro Val Tyr Lys Ala Leu Asn Thr Leu Asp Tyr Thr Val Gly
                        100                 105                 110
        Thr Leu Gly Asn His Glu Phe Asn Tyr Gly Leu Asp Tyr Leu Lys Asn
                        115                 120                 125
        Ala Leu Ala Gly Ala Lys Phe Pro Tyr Val Asn Ala Asn Val Ile Asp
                130                 135                 140
        Ala Arg Thr Lys Gln Pro Met Phe Thr Pro Tyr Leu Ile Lys Asp Thr
        145                 150                 155                 160
        Glu Val Val Asp Lys Asp Gly Lys Lys Gln Thr Leu Lys Ile Gly Tyr
                        165                 170                 175
        Ile Gly Val Val Pro Pro Gln Ile Met Gly Trp Asp Lys Ala Asn Leu
                        180                 185                 190
        Ser Gly Lys Val Thr Val Asn Asp Ile Thr Glu Thr Val Arg Lys Tyr
                        195                 200                 205
        Val Pro Glu Met Arg Glu Lys Gly Ala Asp Val Val Val Leu Ala
                210                 215                 220
        His Ser Gly Leu Ser Ala Asp Pro Tyr Lys Val Met Ala Glu Asn Ser
        225                 230                 235                 240
        Val Tyr Tyr Leu Ser Glu Ile Pro Gly Val Asn Ala Ile Met Phe Gly
                        245                 250                 255
        His Ala His Ala Val Phe Pro Gly Lys Asp Phe Ala Asp Ile Glu Gly
                        260                 265                 270
        Ala Asp Ile Ala Lys Gly Thr Leu Asn Gly Val Pro Ala Val Met Pro
                275                 280                 285
        Gly Met Trp Gly Asp His Leu Gly Val Val Asp Leu Gln Leu Ser Asn
                290                 295                 300
        Asp Ser Gly Lys Trp Gln Val Thr Gln Ala Lys Ala Glu Ala Arg Pro
        305                 310                 315                 320
        Ile Tyr Asp Ile Ala Asn Lys Lys Ser Leu Ala Ala Glu Asp Ser Lys
                        325                 330                 335
        Leu Val Glu Thr Leu Lys Ala Asp His Asp Ala Thr Arg Gln Phe Val
                        340                 345                 350
        Ser Lys Pro Ile Gly Lys Ser Ala Asp Asn Met Tyr Ser Tyr Leu Ala
                        355                 360                 365
        Leu Val Gln Asp Asp Pro Thr Val Gln Val Val Asn Asn Ala Gln Lys
                370                 375                 380
        Ala Tyr Val Glu His Tyr Ile Gln Gly Asp Pro Asp Leu Ala Lys Leu
        385                 390                 395                 400
        Pro Val Leu Ser Ala Ala Pro Phe Lys Val Gly Gly Arg Lys Asn
                        405                 410                 415
        Asp Pro Ala Ser Tyr Val Glu Val Glu Lys Gly Gln Leu Thr Phe Arg
                        420                 425                 430
        Asn Ala Ala Asp Leu Tyr Leu Tyr Pro Asn Thr Leu Ile Val Val Lys
                435                 440                 445
        Ala Ser Gly Lys Glu Val Lys Glu Trp Leu Glu Cys Ser Ala Gly Gln
                450                 455                 460
        Phe Asn Gln Ile Asp Pro Asn Ser Thr Lys Pro Gln Ser Leu Ile Asn
        465                 470                 475                 480
        Trp Asp Gly Phe Arg Thr Tyr Asn Phe Asp Val Ile Asp Gly Val Asn
                        485                 490                 495
```

-continued

```
Tyr Gln Ile Asp Val Thr Gln Pro Ala Arg Tyr Asp Gly Glu Cys Gln
        500                 505                 510

Met Ile Asn Ala Asn Ala Glu Arg Ile Lys Asn Leu Thr Phe Asn Gly
        515                 520                 525

Lys Pro Ile Asp Pro Asn Ala Met Phe Leu Val Ala Thr Asn Asn Tyr
    530                 535                 540

Arg Ala Tyr Gly Gly Lys Phe Ala Gly Thr Gly Asp Ser His Ile Ala
545                 550                 555                 560

Phe Ala Ser Pro Asp Glu Asn Arg Ser Val Leu Ala Ala Trp Ile Ala
                565                 570                 575

Asp Glu Ser Lys Arg Ala Gly Glu Ile His Pro Ala Ala Asp Asn Asn
            580                 585                 590

Trp Arg Leu Ala Pro Ile Ala Gly Asp Lys Lys Leu Asp Ile Arg Phe
        595                 600                 605

Glu Thr Ser Pro Ser Asp Lys Ala Ala Ala Phe Ile Lys Glu Lys Gly
    610                 615                 620

Gln Tyr Pro Met Asn Lys Val Ala Thr Asp Asp Ile Gly Phe Ala Ile
625                 630                 635                 640

Tyr Gln Val Asp Leu Ser Lys
                645
```

```
<210> SEQ ID NO 7
<211> LENGTH: 26
<212> TYPE: DNA
<213> ORGANISM: Artificial Sequence
<220> FEATURE:
<223> OTHER INFORMATION: Primer P1

<400> SEQUENCE: 7
ataagatctg ctgccgaacc cgccaa                                    26

<210> SEQ ID NO 8
<211> LENGTH: 59
<212> TYPE: DNA
<213> ORGANISM: Artificial Sequence
<220> FEATURE:
<223> OTHER INFORMATION: Primer P2

<400> SEQUENCE: 8
ataaagcttg gatccgagct cgaggcggcc gccagggctg catcgacagt ctgacgacc  59

<210> SEQ ID NO 9
<211> LENGTH: 900
<212> TYPE: DNA
<213> ORGANISM: Artificial Sequence
<220> FEATURE:
<223> OTHER INFORMATION: DNA fragment harboring CDS encoding (D69-N356)
      fragment of mutant 2-O-sulfotransferase (Y94A)

<400> SEQUENCE: 9
gcggccgcgc agactaatgc agcagcggat gaagaagaag atatcgtcat tatctataac   60
cgtgttccga aaccgcaag caccagcttt accaatattg cagcagatct gtgcgccaaa   120
aatcgctatc atgtgctgca tattaacacc accaaaaata cccggttat gagcctgcag    180 gatcaggttc gttttgttaa aaacattacc acctggaacg aaatgaaacc gggttttat    240 catggccata tcagctatct ggattttgcg aaatttggcg tgaaaaaaaa accgatctac   300
atcaacgtta ttcgcgatcc gattgaacgt ctggttagct attattactt tctgcgcttc   360
ggtgatgatt atcgtccggg tctgcgtcgt cgtaaacagg gcgacaaaaa aaccttttgat   420
```

```
gaatgtgttg ccgaaggtgg tagcgattgt gcaccggaaa aactgtggct gcagattccg    480 ttttttgcg gtcatagcag cgaatgttgg aatgttggta gccgttgggc aatggatcag     540
gccaaatata acctgatcaa cgaatatttt ctggtgggtg tgaccgaaga actggaagat    600
ttcattatgc tgctggaagc agcactgcct cgttttttc gtggtgcaac cgatctgtat     660
cgtaccggta aaaaagcca tctgcgtaaa acgacggaaa aaaactgcc gaccaaacag      720 accattgcaa aactgcagca gagcgatatt tggaaaatgg aaaacgagtt ttatgaattt    780
gccctggaac agtttcagtt tattcgtgca catgcagttc gtgaaaaaga tggtgatctg    840
tatattctgg cccagaactt cttctacgaa aaatctatc cgaaaagcaa ttaactcgag     900
```

<210> SEQ ID NO 10
<211> LENGTH: 288
<212> TYPE: PRT
<213> ORGANISM: Artificial Sequence
<220> FEATURE:
<223> OTHER INFORMATION: (D69-N356) fragment of mutant
      2-O-sulfotransferase (Y94A)

<400> SEQUENCE: 10

```
Asp Glu Glu Glu Asp Ile Val Ile Ile Tyr Asn Arg Val Pro Lys Thr
1               5                   10                  15

Ala Ser Thr Ser Phe Thr Asn Ile Ala Ala Asp Leu Cys Ala Lys Asn
            20                  25                  30

Arg Tyr His Val Leu His Ile Asn Thr Thr Lys Asn Asn Pro Val Met
        35                  40                  45

Ser Leu Gln Asp Gln Val Arg Phe Val Lys Asn Ile Thr Thr Trp Asn
    50                  55                  60

Glu Met Lys Pro Gly Phe Tyr His Gly His Ile Ser Tyr Leu Asp Phe
65                  70                  75                  80

Ala Lys Phe Gly Val Lys Lys Pro Ile Tyr Ile Asn Val Ile Arg
            85                  90                  95

Asp Pro Ile Glu Arg Leu Val Ser Tyr Tyr Phe Leu Arg Phe Gly
        100                 105                 110

Asp Asp Tyr Arg Pro Gly Leu Arg Arg Lys Gln Gly Asp Lys Lys
        115                 120                 125

Thr Phe Asp Glu Cys Val Ala Glu Gly Gly Ser Asp Cys Ala Pro Glu
130                 135                 140

Lys Leu Trp Leu Gln Ile Pro Phe Phe Cys Gly His Ser Ser Glu Cys
145                 150                 155                 160

Trp Asn Val Gly Ser Arg Trp Ala Met Asp Gln Ala Lys Tyr Asn Leu
            165                 170                 175

Ile Asn Glu Tyr Phe Leu Val Gly Val Thr Glu Glu Leu Glu Asp Phe
        180                 185                 190

Ile Met Leu Leu Glu Ala Ala Leu Pro Arg Phe Phe Arg Gly Ala Thr
        195                 200                 205

Asp Leu Tyr Arg Thr Gly Lys Lys Ser His Leu Arg Lys Thr Thr Glu
        210                 215                 220

Lys Lys Leu Pro Thr Lys Gln Thr Ile Ala Lys Leu Gln Gln Ser Asp
225                 230                 235                 240

Ile Trp Lys Met Glu Asn Glu Phe Tyr Glu Phe Ala Leu Glu Gln Phe
            245                 250                 255

Gln Phe Ile Arg Ala His Ala Val Arg Glu Lys Asp Gly Asp Leu Tyr
        260                 265                 270
```

Ile Leu Ala Gln Asn Phe Phe Tyr Glu Lys Ile Tyr Pro Lys Ser Asn
            275                 280                 285

<210> SEQ ID NO 11
<211> LENGTH: 1881
<212> TYPE: DNA
<213> ORGANISM: Artificial Sequence
<220> FEATURE:
<223> OTHER INFORMATION: DNA fragment encoding N-tag 6xHis-SUMO peptide
      fused with (G70-N585) fragment of HNSG-5epi native to Danio rerio

<400> SEQUENCE: 11

| | | | | |
|---|---|---|---|---|
| catatgcatc | atcaccacca | tcacgggtcc | ctgcaggact | cagaagtcaa tcaagaagct | 60 |
| aagccagagg | tcaagccaga | agtcaagcct | gagactcaca | tcaatttaaa ggtgtccgat | 120 |
| ggatcttcag | agatcttctt | caagatcaaa | aagaccactc | ctttaagaag gctgatggaa | 180 |
| gcgttcgcta | aaagacaggg | taaggaaatg | gactccttaa | cgttcttgta cgacggtatt | 240 |
| gaaattcaag | ctgatcagac | ccctgaagat | ttggacatgg | aggataacga tattattgag | 300 |
| gctcaccgcg | aacagattgg | aggtggcgtt | cggtatgaag | aaatcgactg cttgattaac | 360 |
| gacgatgcaa | ccatcaaagg | cgccgcgaaa | ggctctgagg | tgtacatgcc gtttagctgg | 420 |
| atggaaaagt | atttcgaagt | gtacggcaaa | gttgtgcaat | acgatggcta tgatcgcttt | 480 |
| gaattctctc | attcatacag | caaagtgtat | gcgcagcgcg | agcagtatca tccgaatggt | 540 |
| gtctttatga | gctttgaggg | gtataacgta | gaagtgcgcg | atcgtgtcaa atgtatctcc | 600 |
| ggtgttgaag | gtgttccgct | agcacccag | tggggtccac | agggctactt tatgcgatt | 660 |
| cagattgccc | agtacggtct | gtcgcactat | tcgaagaact | taaccgaacg tccgccgcat | 720 |
| gtggaggtgt | atgatacggc | ggaagaacgc | gacagtcgta | gttctgcctg gaccgttcca | 780 |
| aaaggatgct | cactgacccg | cgtttacgac | aaaacccgcg | cgacaagcgt ccgcgaattt | 840 |
| agcgctccgg | aaaatagcga | aggagttagc | ttaccacttg | gtaacaccaa agatttcatt | 900 |
| atctcctttg | acctgaaatt | cacaagtaat | gggtcagtct | ctgtgatttt ggagactact | 960 |
| gaaaagggac | cgccgtttgt | gatccactat | gtcaccacga | cgcagttgat ccttctgaaa | 1020 |
| gatcgtgaca | ttacctacgg | gattggtcca | cgcacgacct | ggacaactgt aacccgggat | 1080 |
| ctgctgacgg | acttacgcaa | aggtatcggc | cttagcaaca | cgaaggcagt aaaagcaacc | 1140 |
| aaaaccatgc | cgcgccgtgt | ggtaaaactg | gtcgtacatg | gcacgggtac cattgacaac | 1200 |
| atcaccatta | gcaccacgtc | ccatatggcc | gcctttatg | ccgcgtctga ttggttggtg | 1260 |
| cgcaatcagg | atgaacgtgg | tggctggccg | attatggtca | cccgcaaatt aggcgagggc | 1320 |
| ttccgtgcct | tggaaccggg | ctggtattcc | gcgatggcgc | agggccaagc gatgtccact | 1380 |
| ctggtgcgtg | cctatctcat | gacgaaagac | gatcgttatc | tgaaagcggc gctgcgtgca | 1440 |
| actggcccttt | ttaagctgcc | gtcagaacag | cacggagtga | aagcggtgtt tatgaacaaa | 1500 |
| tacgattggt | acgaagagta | tccgacaatc | cctagttcct | ttgtcctgaa cggtttcatc | 1560 |
| tattcactta | ttggcctgtt | tgatctggca | cagactgctg | gcgagaaact gggccgtgat | 1620 |
| gcgggtcagc | tctacagcaa | ggggatggag | tctctgaaag | ttatgttacc gctctacgat | 1680 |
| acagggtcgg | ggaccatcta | tgatctccgc | cacttcattc | tgggaacagc tcccaatctg | 1740 |
| gcacgttggg | attaccacac | cacgcatatt | aatcagctgc | aactgctggg tactatcgat | 1800 |
| aatagtccga | ttttccgcga | ctcggtcaaa | cgctggaaat | cgtacctgaa aggcggtcgc | 1860 |
| gcaaagcata | attaactcga | g | | | 1881 |

-continued

```
<210> SEQ ID NO 12
<211> LENGTH: 107
<212> TYPE: PRT
<213> ORGANISM: Artificial Sequence
<220> FEATURE:
<223> OTHER INFORMATION: N-tagged 6xHis-SUMO peptide

<400> SEQUENCE: 12

Met His His His His His Gly Ser Leu Gln Asp Ser Glu Val Asn
1               5                   10                  15

Gln Glu Ala Lys Pro Glu Val Lys Pro Glu Val Lys Pro Glu Thr His
            20                  25                  30

Ile Asn Leu Lys Val Ser Asp Gly Ser Ser Glu Ile Phe Phe Lys Ile
            35                  40                  45

Lys Lys Thr Thr Pro Leu Arg Arg Leu Met Glu Ala Phe Ala Lys Arg
50                  55                  60

Gln Gly Lys Glu Met Asp Ser Leu Thr Phe Leu Tyr Asp Gly Ile Glu
65                  70                  75                  80

Ile Gln Ala Asp Gln Thr Pro Glu Asp Leu Asp Met Glu Asp Asn Asp
                85                  90                  95

Ile Ile Glu Ala His Arg Glu Gln Ile Gly Gly
            100                 105

<210> SEQ ID NO 13
<211> LENGTH: 516
<212> TYPE: PRT
<213> ORGANISM: Artificial Sequence
<220> FEATURE:
<223> OTHER INFORMATION: (G70-N585) fragment of HNSG-5epi native to
      Danio rerio

<400> SEQUENCE: 13

Gly Val Arg Tyr Glu Glu Ile Asp Cys Leu Ile Asn Asp Asp Ala Thr
1               5                   10                  15

Ile Lys Gly Arg Arg Glu Gly Ser Glu Val Tyr Met Pro Phe Ser Trp
            20                  25                  30

Met Glu Lys Tyr Phe Glu Val Tyr Gly Lys Val Val Gln Tyr Asp Gly
            35                  40                  45

Tyr Asp Arg Phe Glu Phe Ser His Ser Tyr Ser Lys Val Tyr Ala Gln
50                  55                  60

Arg Glu Gln Tyr His Pro Asn Gly Val Phe Met Ser Phe Glu Gly Tyr
65                  70                  75                  80

Asn Val Glu Val Arg Asp Arg Val Lys Cys Ile Ser Gly Val Glu Gly
                85                  90                  95

Val Pro Leu Ser Thr Gln Trp Gly Pro Gln Gly Tyr Phe Tyr Ala Ile
            100                 105                 110

Gln Ile Ala Gln Tyr Gly Leu Ser His Tyr Ser Lys Asn Leu Thr Glu
            115                 120                 125

Arg Pro Pro His Val Glu Val Tyr Asp Thr Ala Glu Glu Arg Asp Ser
            130                 135                 140

Arg Ser Ser Ala Trp Thr Val Pro Lys Gly Cys Ser Leu Thr Arg Val
145                 150                 155                 160

Tyr Asp Lys Thr Arg Ala Thr Ser Val Arg Glu Phe Ser Ala Pro Glu
                165                 170                 175

Asn Ser Glu Gly Val Ser Leu Pro Leu Gly Asn Thr Lys Asp Phe Ile
            180                 185                 190

Ile Ser Phe Asp Leu Lys Phe Thr Ser Asn Gly Ser Val Ser Val Ile
            195                 200                 205
```

| Leu | Glu | Thr | Thr | Glu | Lys | Gly | Pro | Pro | Phe | Val | Ile | His | Tyr | Val | Thr |
|---|---|---|---|---|---|---|---|---|---|---|---|---|---|---|---|
| | 210 | | | | 215 | | | | | 220 | | | | | |

Thr Thr Gln Leu Ile Leu Lys Asp Arg Asp Ile Thr Tyr Gly Ile
225                 230                 235                 240

Gly Pro Arg Thr Thr Trp Thr Val Thr Arg Asp Leu Leu Thr Asp
            245                 250                 255

Leu Arg Lys Gly Ile Gly Leu Ser Asn Thr Lys Ala Val Lys Ala Thr
        260                 265                 270

Lys Thr Met Pro Arg Arg Val Val Lys Leu Val Val His Gly Thr Gly
        275                 280                 285

Thr Ile Asp Asn Ile Thr Ile Ser Thr Thr Ser His Met Ala Ala Phe
290                 295                 300

Tyr Ala Ala Ser Asp Trp Leu Val Arg Asn Gln Asp Glu Arg Gly Gly
305                 310                 315                 320

Trp Pro Ile Met Val Thr Arg Lys Leu Gly Glu Gly Phe Arg Ala Leu
            325                 330                 335

Glu Pro Gly Trp Tyr Ser Ala Met Ala Gln Gly Gln Ala Met Ser Thr
            340                 345                 350

Leu Val Arg Ala Tyr Leu Met Thr Lys Asp Asp Arg Tyr Leu Lys Ala
        355                 360                 365

Ala Leu Arg Ala Thr Gly Pro Phe Lys Leu Pro Ser Glu Gln His Gly
370                 375                 380

Val Lys Ala Val Phe Met Asn Lys Tyr Asp Trp Tyr Glu Glu Tyr Pro
385                 390                 395                 400

Thr Ile Pro Ser Ser Phe Val Leu Asn Gly Phe Ile Tyr Ser Leu Ile
            405                 410                 415

Gly Leu Phe Asp Leu Ala Gln Thr Ala Gly Glu Lys Leu Gly Arg Asp
            420                 425                 430

Ala Gly Gln Leu Tyr Ser Lys Gly Met Glu Ser Leu Lys Val Met Leu
        435                 440                 445

Pro Leu Tyr Asp Thr Gly Ser Gly Thr Ile Tyr Asp Leu Arg His Phe
450                 455                 460

Ile Leu Gly Thr Ala Pro Asn Leu Ala Arg Trp Asp Tyr His Thr Thr
465                 470                 475                 480

His Ile Asn Gln Leu Gln Leu Leu Gly Thr Ile Asp Asn Ser Pro Ile
            485                 490                 495

Phe Arg Asp Ser Val Lys Arg Trp Lys Ser Tyr Leu Lys Gly Gly Arg
            500                 505                 510

Ala Lys His Asn
        515

<210> SEQ ID NO 14
<211> LENGTH: 895
<212> TYPE: DNA
<213> ORGANISM: Artificial Sequence
<220> FEATURE:
<223> OTHER INFORMATION: DNA fragment encoding N-tag 6xHis leader fused
      with ST1A1 native to Rattus norvegicus

<400> SEQUENCE: 14
gaattcgatg gaattttcac gtccgcctct ggttcatgtt aaaggtattc cgctgattaa    60
atacttcgcc gaaaccattg gtccgctgca gaattttacc gcatggcctg atgatctgct   120
gattagcacc tatccgaaaa gcggcaccac ctggatgagc gaaattctgg atatgattta   180
tcagggtggc aaactggaaa atgtgggtcg tgcaccgatt tatgcacgtg ttccgtttct   240

```
ggaatttaaa tgtccggggtg ttccgagcgg tctggaaacc ctggaagaaa caccggcacc    300
gcgtctgctg aaaacccatc tgccgctgag cctgctgccg cagtcactgc tggatcagaa    360
agttaaagtt atctatattg cccgtaacgc caaagatgtt gtggtgagct attataactt    420
ctataacatg gcaaaactgc atccggatcc tggcacctgg gatagctttc tggaaaactt    480
tatggatggt gaagttagct atggtagctg gtatcagcat gtgaaagaat ggtgggaact    540
gcgtcatacc catccggttc tgtacctgtt ttatgaagat atcaaagaga acccgaaacg    600
cgaaatcaaa aaaatcctgg aatttctggg tcgtagcctg ccggaagaaa ccgttgatag    660
cattgttcat cataccagct tcaaaaaaat gaaagaaaac tgcatgacca actacaccac    720
cattccgacc gaaattatgg atcacaatgt tagcccgttt atgcgtaaag gcaccaccgg    780
tgattggaaa aatacattta ccgttgcaca gaacgaacgc tttgatgcac attatgcaaa    840
aaccatgacc gactgcgatt tcaaatttcg ttgtgaactg taagtcgaca agctt         895

<210> SEQ ID NO 15
<211> LENGTH: 31
<212> TYPE: DNA
<213> ORGANISM: Artificial Sequence
<220> FEATURE:
<223> OTHER INFORMATION: Primer P3

<400> SEQUENCE: 15
aatatcatat gggcagcagc catcaccatc a                                   31

<210> SEQ ID NO 16
<211> LENGTH: 34
<212> TYPE: DNA
<213> ORGANISM: Artificial Sequence
<220> FEATURE:
<223> OTHER INFORMATION: Primer P4

<400> SEQUENCE: 16
aatataagct tgtcgactta cagttcacaa cgaa                                34

<210> SEQ ID NO 17
<211> LENGTH: 36
<212> TYPE: DNA
<213> ORGANISM: Artificial Sequence
<220> FEATURE:
<223> OTHER INFORMATION: Primer P5

<400> SEQUENCE: 17
agctgagtcg accccccagga aaaattggtt aataac                             36

<210> SEQ ID NO 18
<211> LENGTH: 33
<212> TYPE: DNA
<213> ORGANISM: Artificial Sequence
<220> FEATURE:
<223> OTHER INFORMATION: Primer P6

<400> SEQUENCE: 18
agctgagcat gcttccaact gcgctaatga cgc                                 33

<210> SEQ ID NO 19
<211> LENGTH: 313
<212> TYPE: DNA
<213> ORGANISM: Artificial Sequence
<220> FEATURE:
<223> OTHER INFORMATION: DNA fragment of Pnlp0 promoter
```

<400> SEQUENCE: 19

```
gcatgcttcc aactgcgcta atgacgcagc tggacgaagg cgggattctc gtcttacccg    60
taggggagga gcaccagtat ttgaaacggg tgcgtcgtcg gggaggcgaa tttattatcg   120
ataccgtgga ggccgtgcgc tttgtccctt tagtgaaggg tgagctggct taaaacgtga   180
ggaaatacct ggattttttcc tggttatttt gccgcaggtc agcgtatcgt gaacatcttt   240
tccagtgttc agtagggtgc cttgcacggt aattatgtca ctggttatta accaattttt   300
cctgggggtc gac                                                      313
```

<210> SEQ ID NO 20
<211> LENGTH: 369
<212> TYPE: DNA
<213> ORGANISM: Artificial Sequence
<220> FEATURE:
<223> OTHER INFORMATION: DNA fragment

<400> SEQUENCE: 20

```
tctagaaaca gaatttgcct ggcggcagta gcgcggtggt cccacctgac ccatgccga     60 actcagaagt gaaacgccgt agcgccgatg gtagtgtggg gtctccccat gcgagagtag   120
ggaactgcca ggcatcaaat aaaacgaaag gctcagtcga aagactgggc ctttcgtttt   180
atctgttgtt tgtcggtgaa cgctctcctg agtaggacaa atccgccggg agcggatttg   240
aacgttgcga agcaacggcc cggagggtgg cgggcaggac gccgccata aactgccagg   300 catcaaatta agcagaaggc catcctgacg gatggccttt ttgcgtttct acaaactctt   360
cctggatcc                                                          369
```

<210> SEQ ID NO 21
<211> LENGTH: 33
<212> TYPE: DNA
<213> ORGANISM: Artificial Sequence
<220> FEATURE:
<223> OTHER INFORMATION: Primer P7

<400> SEQUENCE: 21

```
agctgatcta gaaaacagaa tttgcctggc ggc                                 33
```

<210> SEQ ID NO 22
<211> LENGTH: 33
<212> TYPE: DNA
<213> ORGANISM: Artificial Sequence
<220> FEATURE:
<223> OTHER INFORMATION: Primer P8

<400> SEQUENCE: 22

```
agctgaggat ccaggaagag tttgtagaaa cgc                                 33
```

<210> SEQ ID NO 23
<211> LENGTH: 35
<212> TYPE: DNA
<213> ORGANISM: Artificial Sequence
<220> FEATURE:
<223> OTHER INFORMATION: Primer P9

<400> SEQUENCE: 23

```
ttcctggggg tcgacatgac tacgaaaatt tttaa                               35
```

<210> SEQ ID NO 24
<211> LENGTH: 35
<212> TYPE: DNA
<213> ORGANISM: Artificial Sequence

```
<220> FEATURE:
<223> OTHER INFORMATION: Primer P10

<400> SEQUENCE: 24
attctgtttt ctagactaag gaaccaacac aagct                               35

<210> SEQ ID NO 25
<211> LENGTH: 30
<212> TYPE: DNA
<213> ORGANISM: Artificial Sequence
<220> FEATURE:
<223> OTHER INFORMATION: Primer P11

<400> SEQUENCE: 25 gtcgacccccc aggaaaaatt ggttaataac                                    30

<210> SEQ ID NO 26
<211> LENGTH: 30
<212> TYPE: DNA
<213> ORGANISM: Artificial Sequence
<220> FEATURE:
<223> OTHER INFORMATION: Primer P12

<400> SEQUENCE: 26
tctagaaaac agaatttgcc tggcggcagt                                     30

<210> SEQ ID NO 27
<211> LENGTH: 1980
<212> TYPE: DNA
<213> ORGANISM: Flavobacterium heparinum

<400> SEQUENCE: 27
atgactacga aaattttaa aaggatcatt gtatttgctg taattgccct atcgtcggga      60
aatatacttg cacaaagctc ttccattacc aggaaagatt ttgaccacat caaccttgag    120
tattccggac tggaaaaggt taataaagca gttgctgccg gcaactatga cgatgcggcc    180
aaagcattac tggcatacta cagggaaaaa agtaaggcca gggaacctga tttcagtaat    240
gcagaaaagc ctgccgatat acgccagccc atagataagg ttacgcgtga atggccgac    300 aaggctttgg tccaccagtt tcaaccgcac aaaggctacg ctatttttga ttatggtaaa    360
gacatcaact ggcagatgtg gccggtaaaa gacaatgaag tacgctggca gttgcaccgt    420
gtaaaatggt ggcaggctat ggccctggtt tatcacgcta cgggcgatga aaaatatgca    480
agagaatggg tatatcagta cagcgattgg gccagaaaaa acccattggg cctgtcgcag    540
gataatgata aatttgtgtg gcggccccttt gaagtgtcgg acagggtaca agtcttccc    600 ccaaccttca gcttatttgt aaactcgcca gcctttaccc cagccttttt aatggaattt    660
ttaaacagtt accaccaaca ggccgattat ttatctacgc attatgccga acagggaaac    720
caccgtttat ttgaagccca acgcaacttg tttgcagggg tatctttccc tgaatttaaa    780
gattcaccaa gatggaggca aaccggcata tcggtgctga acaccgagat caaaaaacag    840
gtttatgccg atgggatgca gtttgaactt tcaccaattt accatgtagc tgccatcgat    900
atcttcttaa aggcctatgg ttctgcaaaa cgagttaacc ttgaaaaaga atttccgcaa    960
tcttatgtac aaactgtaga aaatatgatt atggcgctga tcagtatttc actgccagat   1020
tataacaccc ctatgtttgg agattcatgg attacagata aaatttcag gatggcacag   1080 tttgccagct gggcccggggt tttcccggca aaccaggcca taaaatattt tgctacagat   1140
ggcaaacaag gtaaggcgcc taactttta tccaaagcat tgagcaatgc aggcttttat    1200
```

```
acgtttagaa gcggatggga taaaaatgca accgttatgg tattaaaagc cagtcctccc    1260
ggagaatttc atgcccagcc ggataacggg actttttgaac ttttttataaa gggcagaaac    1320 tttaccccag acgccggggt atttgtgtat agcggcgacg aagccatcat gaaactgcgg    1380
aactggtacc gtcaaacccg catacacagc acgcttacac tcgacaatca aaatatggtc    1440
attaccaaag cccggcaaaa caaatgggaa acaggaaata accttgatgt gcttacctat    1500
accaacccaa gctatccgaa tctggaccat cagcgcagtg tacttttcat caacaaaaaa    1560
tactttctgg tcatcgatag gcaataggc gaagctaccg gaaacctggg cgtacactgg    1620
cagcttaaag aagacagcaa ccctgttttc gataagacaa agaaccgggt ttacaccact    1680
tacagagatg gtaacaacct gatgatccaa tcgttgaatg cggacaggac cagcctcaat    1740
gaagaagaag gaaaggtatc ttatgtttac aataaggagc tgaaaagacc tgctttcgta    1800
tttgaaaagc ctaaaaagaa tgccggcaca caaaattttg tcagtatagt ttatccatac    1860
gacggccaga aggctccaga gatcagcata cgggaaaaca agggcaatga ttttgagaaa    1920
ggcaagctta atctaaccct taccattaac ggaaaacaac agcttgtgtt ggttccttag    1980
```

<210> SEQ ID NO 28
<211> LENGTH: 659
<212> TYPE: PRT
<213> ORGANISM: Flavobacterium heparinum

<400> SEQUENCE: 28

```
Met Thr Thr Lys Ile Phe Lys Arg Ile Ile Val Phe Ala Val Ile Ala
1               5                  10                  15

Leu Ser Ser Gly Asn Ile Leu Ala Gln Ser Ser Ile Thr Arg Lys
            20                  25                  30

Asp Phe Asp His Ile Asn Leu Glu Tyr Ser Gly Leu Glu Lys Val Asn
        35                  40                  45

Lys Ala Val Ala Ala Gly Asn Tyr Asp Asp Ala Ala Lys Ala Leu Leu
    50                  55                  60

Ala Tyr Tyr Arg Glu Lys Ser Lys Ala Arg Glu Pro Asp Phe Ser Asn
65                  70                  75                  80

Ala Glu Lys Pro Ala Asp Ile Arg Gln Pro Ile Asp Lys Val Thr Arg
                85                  90                  95

Glu Met Ala Asp Lys Ala Leu Val His Gln Phe Gln Pro His Lys Gly
            100                 105                 110

Tyr Gly Tyr Phe Asp Tyr Gly Lys Asp Ile Asn Trp Gln Met Trp Pro
        115                 120                 125

Val Lys Asp Asn Glu Val Arg Trp Gln Leu His Arg Val Lys Trp Trp
    130                 135                 140

Gln Ala Met Ala Leu Val Tyr His Ala Thr Gly Asp Glu Lys Tyr Ala
145                 150                 155                 160

Arg Glu Trp Val Tyr Gln Tyr Ser Asp Trp Ala Arg Lys Asn Pro Leu
                165                 170                 175

Gly Leu Ser Gln Asp Asn Asp Lys Phe Val Trp Arg Pro Leu Glu Val
            180                 185                 190

Ser Asp Arg Val Gln Ser Leu Pro Pro Thr Phe Ser Leu Phe Val Asn
        195                 200                 205

Ser Pro Ala Phe Thr Pro Ala Phe Leu Met Glu Phe Leu Asn Ser Tyr
    210                 215                 220

His Gln Gln Ala Asp Tyr Leu Ser Thr His Tyr Ala Glu Gln Gly Asn
225                 230                 235                 240
```

-continued

```
His Arg Leu Phe Glu Ala Gln Arg Asn Leu Phe Ala Gly Val Ser Phe
                245                 250                 255

Pro Glu Phe Lys Asp Ser Pro Arg Trp Arg Gln Thr Gly Ile Ser Val
            260                 265                 270

Leu Asn Thr Glu Ile Lys Lys Gln Val Tyr Ala Asp Gly Met Gln Phe
        275                 280                 285

Glu Leu Ser Pro Ile Tyr His Val Ala Ala Ile Asp Ile Phe Leu Lys
    290                 295                 300

Ala Tyr Gly Ser Ala Lys Arg Val Asn Leu Glu Lys Glu Phe Pro Gln
305                 310                 315                 320

Ser Tyr Val Gln Thr Val Glu Asn Met Ile Met Ala Leu Ile Ser Ile
                325                 330                 335

Ser Leu Pro Asp Tyr Asn Thr Pro Met Phe Gly Asp Ser Trp Ile Thr
            340                 345                 350

Asp Lys Asn Phe Arg Met Ala Gln Phe Ala Ser Trp Ala Arg Val Phe
        355                 360                 365

Pro Ala Asn Gln Ala Ile Lys Tyr Phe Ala Thr Asp Gly Lys Gln Gly
    370                 375                 380

Lys Ala Pro Asn Phe Leu Ser Lys Ala Leu Ser Asn Ala Gly Phe Tyr
385                 390                 395                 400

Thr Phe Arg Ser Gly Trp Asp Lys Asn Ala Thr Val Met Val Leu Lys
                405                 410                 415

Ala Ser Pro Pro Gly Glu Phe His Ala Gln Pro Asp Asn Gly Thr Phe
            420                 425                 430

Glu Leu Phe Ile Lys Gly Arg Asn Phe Thr Pro Asp Ala Gly Val Phe
        435                 440                 445

Val Tyr Ser Gly Asp Glu Ala Ile Met Lys Leu Arg Asn Trp Tyr Arg
    450                 455                 460

Gln Thr Arg Ile His Ser Thr Leu Thr Leu Asp Asn Gln Asn Met Val
465                 470                 475                 480

Ile Thr Lys Ala Arg Gln Asn Lys Trp Glu Thr Gly Asn Asn Leu Asp
                485                 490                 495

Val Leu Thr Tyr Thr Asn Pro Ser Tyr Pro Asn Leu Asp His Gln Arg
            500                 505                 510

Ser Val Leu Phe Ile Asn Lys Lys Tyr Phe Leu Val Ile Asp Arg Ala
        515                 520                 525

Ile Gly Glu Ala Thr Gly Asn Leu Gly Val His Trp Gln Leu Lys Glu
    530                 535                 540

Asp Ser Asn Pro Val Phe Asp Lys Thr Lys Asn Arg Val Tyr Thr Thr
545                 550                 555                 560

Tyr Arg Asp Gly Asn Asn Leu Met Ile Gln Ser Leu Asn Ala Asp Arg
                565                 570                 575

Thr Ser Leu Asn Glu Glu Gly Lys Val Ser Tyr Val Tyr Asn Lys
            580                 585                 590

Glu Leu Lys Arg Pro Ala Phe Val Phe Glu Lys Pro Lys Lys Asn Ala
        595                 600                 605

Gly Thr Gln Asn Phe Val Ser Ile Val Tyr Pro Tyr Asp Gly Gln Lys
    610                 615                 620
```

```
Ala Pro Glu Ile Ser Ile Arg Glu Asn Lys Gly Asn Asp Phe Glu Lys
625                 630                 635                 640

Gly Lys Leu Asn Leu Thr Leu Thr Ile Asn Gly Lys Gln Gln Leu Val
                645                 650                 655

Leu Val Pro
```